(12) United States Patent
Herrick et al.

(10) Patent No.: US 12,611,546 B2
(45) Date of Patent: *Apr. 28, 2026

(54) METHODS AND SYSTEMS OF USING [[PEMF]] ELECTROMAGNETIC FIELD STIMULATION TO INCREASE HEAT SHOCK PROTEIN EXPRESSION IN A MAMMAL

(71) Applicant: Electro Cellular Healthcare Solutions LLC, Boca Raton, FL (US)

(72) Inventors: Norton Herrick, Boca Raton, FL (US); Miles Herrick, Cedar Knolls, NJ (US); Sean Hagberg, Cranston, RI (US); David Muehsam, New York, NY (US); David Saloff, Pacific Palisades, CA (US)

(73) Assignee: Electro Cellular Healthcare Solutions LLC, Boca Raton, FL (US)

( * ) Notice: Subject to any disclaimer, the term of this patent is extended or adjusted under 35 U.S.C. 154(b) by 1064 days.

This patent is subject to a terminal disclaimer.

(21) Appl. No.: 17/567,077

(22) Filed: Dec. 31, 2021

(65) Prior Publication Data

US 2022/0370815 A1     Nov. 24, 2022

Related U.S. Application Data

(63) Continuation-in-part of application No. 17/327,279, filed on May 21, 2021, now Pat. No. 11,998,754.

(51) Int. Cl.
A61N 2/00      (2006.01)
A61N 2/02      (2006.01)

(52) U.S. Cl.
CPC ............... A61N 2/004 (2013.01); A61N 2/02 (2013.01)

(58) Field of Classification Search
None
See application file for complete search history.

(56) References Cited

U.S. PATENT DOCUMENTS 9,415,233 B2     8/2016  Pilla
2015/0297910 A1*  10/2015  Dimino ................. A42B 1/242
600/14

(Continued)

FOREIGN PATENT DOCUMENTS

| CN | 201708773 U | 1/2011 |
| GB | 2162066 A | 1/1986 |
| WO | 2016178631 A1 | 11/2016 |

OTHER PUBLICATIONS

Gaynor, J. S., Hagberg, S., & Gurfein, B. T. (2018). Veterinary applications of pulsed electromagnetic field therapy. Research in Veterinary Science, 119, 1-8. https://doi.org/10.1016/j.rvsc.2018.05.005 (Year: 2018).*

(Continued)

*Primary Examiner* — Charles A Marmor, II
*Assistant Examiner* — Marc D. Honrath
(74) *Attorney, Agent, or Firm* — Blank Rome LLP

(57)     ABSTRACT

Methods and devices for increasing heat shock protein expression, reducing inflammation, reducing pro-inflammatory cytokines molecules and increasing anti-inflammatory signaling molecules in a mammal is provided. In at least one embodiment, a device comprising, a power supply; an amplifier; an antenna and a waveform generator is provided and the one or more signals have an aperiodic continuous waveform function or an aperiodic pulse train that increase heat shock protein expression, reduce inflammation, reduce pro-inflammatory cytokines molecules and/or increases anti-inflammatory signaling molecules in a mammal.

14 Claims, 31 Drawing Sheets

(56)                    References Cited

U.S. PATENT DOCUMENTS

| 2018/0043174 A1 | 2/2018 | Gurfein |
| 2020/0001101 A1 | 1/2020 | Moffett |
| 2022/0370815 A1 | 11/2022 | Herrick et al. |

OTHER PUBLICATIONS

Wikimedia Foundation. (Apr. 24, 2021). Pulse wave. Wikipedia. https://en.wikipedia.org/w/index.php?title=Pulse_wave&oldid= 1019695026 (Year: 2021).*

Moseley, P. L. (1998). Heat shock proteins and the inflammatory response. Annals of the New York Academy of Sciences, 856(1), 206-213. https://doi.org/10.1111/j.17 49-6632.1998.tb08327.x (Year: 1998).

Moffett, J., Kubat, N., Fray, L. (2015). Effect of pulsed electromagnetic field treatment on programmed resolution of inflammation pathway markers in human cells in culture. Journal of Inflammation Research, 59. https://doi.org/10.2147/jir.s78631 (Year: 2015).

The Mathworks Inc.: "Optimization Toolbox version: 9.4 (R2022b)," 2018, 7 Pages, Natick, Massachusetts, Retrieved from URL: https://www.mathworks.com.

* cited by examiner

FIG. 1

| waveform | peak (µT) | mVpp | Signal Class |
|---|---|---|---|
| R1 | 5 | 156 | reference |
| S1 | 5 | 156 | R |
| S2 | 10 | 312 | R |
| S3 | 15 | 468 | R |
| S4 | 2 | 63 | A |
| S5 | 4 | 125 | A |
| S6 | 10 | 10 | A |
| S7 | 15 | 15 | A |
| S8 | 5 | 156 | DR |
| S9 | 10 | 312 | DR |
| S10 | 15 | 468 | DR |

FIG. 7

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.00083 | 4.38E-07 | 0.0006431 | 0.03028 | 4.18E-05 | 0.00027571 | 0.05762 | 0.018641 | 0.0003882 |
| 0.00231 | 6.81E-06 | 0.0007325 | 0.03133 | 0.0011231 | 0.00062385 | 0.05859 | 0.075779 | 0.00047275 |
| 0.00325 | 2.34E-07 | 0.00028789 | 0.03222 | 5.03E-05 | 0.00030169 | 0.05927 | 0.014078 | 0.00024838 |
| 0.00414 | 2.86E-06 | 0.00047516 | 0.03313 | 0.00035753 | 0.00049121 | 0.06001 | 0.19698 | 0.00040765 |
| 0.0049 | 1.95E-06 | 0.000035492 | 0.03391 | 0.00020961 | 0.0003578 | 0.06077 | 0.27019 | 0.00064833 |
| 0.00598 | 2.30E-05 | 0.00060274 | 0.03506 | 0.0027104 | 0.00072162 | 0.06189 | 0.30954 | 0.000090639 |
| 0.00681 | 1.66E-07 | 0.00018068 | 0.03665 | 0.0033644 | 0.00080165 | 0.0631 | 0.19145 | 0.00074421 |
| 0.00771 | 1.49E-05 | 0.00053529 | 0.03783 | 0.0011806 | 0.00079673 | 0.06468 | 0.14182 | 0.00075367 |
| 0.00856 | 1.18E-05 | 0.00041155 | 0.03938 | 0.0066723 | 0.000077183 | 0.06586 | 0.0032327 | 0.00030129 |
| 0.00969 | 6.70E-05 | 0.00065929 | 0.0405 | 3.47E-06 | 0.00010721 | 0.06659 | 0.0089014 | 0.00047551 |
| 0.01133 | 0.00021141 | 0.00078846 | 0.04117 | 0.0011098 | 0.00050281 | 0.06753 | 0.0022815 | 0.00035899 |
| 0.01245 | 9.05E-06 | 0.00051985 | 0.04217 | 0.00067131 | 0.00041132 | 0.06844 | 0.020153 | 0.00062305 |
| 0.01404 | 0.00037765 | 0.00079521 | 0.0431 | 0.0033402 | 0.0006275 | 0.06947 | 0.00023656 | 0.00021377 |
| 0.01575 | 0.00010797 | 0.00057058 | 0.04405 | 2.36E-06 | 9.40E-05 | 0.07018 | 0.0052481 | 0.00049811 |
| 0.01681 | 5.29E-05 | 0.00042723 | 0.0448 | 0.0030287 | 0.0005431 | 0.07118 | 0.0023676 | 0.00041777 |
| 0.01772 | 0.00013663 | 0.00059814 | 0.04584 | 0.0015765 | 0.00042469 | 0.07216 | 0.0099017 | 0.00077117 |
| 0.01862 | 4.47E-09 | 4.15E-05 | 0.04678 | 0.0041854 | 0.000069551 | 0.07379 | 0.017048 | 0.00074472 |
| 0.01942 | 0.00023832 | 0.0005825 | 0.04849 | 0.025241 | 0.00078439 | 0.07503 | 0.0011786 | 0.00042689 |
| 0.02048 | 7.28E-05 | 0.000040384 | 0.04963 | 5.17E-07 | 5.09E-05 | 0.07664 | 0.012407 | 0.00079708 |
| 0.02134 | 0.00012611 | 0.000055946 | 0.05012 | 0.00096124 | 0.00033139 | 0.07839 | 0.0017215 | 0.00063763 |
| 0.02314 | 0.0011608 | 0.000081551 | 0.05135 | 0.042442 | 0.0007567 | 0.07929 | 0.00081974 | 0.00042013 |
| 0.02474 | 0.00028329 | 0.000054148 | 0.053 | 0.021189 | 0.00072913 | 0.08035 | 0.0019046 | 0.00055929 |
| 0.02599 | 0.0012667 | 0.00072071 | 0.05395 | 0.007823 | 0.00042681 | 0.08111 | 5.35E-08 | 4.32E-05 |
| 0.02759 | 0.001052 | 0.0008112 | 0.05498 | 0.020519 | 0.000051323 | 0.08205 | 0.0016698 | 0.00061863 |
| 0.0286 | 0.00011902 | 0.0003901 | 0.05569 | 0.00033894 | 0.00016994 | 0.08297 | 0.00045121 | 0.0004219 |
| 0.02956 | 0.00027396 | 0.000047985 | 0.05672 | 0.086376 | 0.00061466 | 0.08399 | 0.00077482 | 0.00052504 |

FIG. 8

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.08575 | 0.0040521 | 0.00078063 | 0.11377 | 4.17E-05 | 0.00076594 | 0.14286 | 0.00038285 | 0.00061165 |
| 0.08731 | 0.00041125 | 0.00072985 | 0.11544 | 5.72E-06 | 0.00062894 | 0.14379 | 7.28E-11 | 1.52E-05 |
| 0.08848 | 0.0023036 | 0.00080039 | 0.11655 | 6.81E-07 | 0.00042116 | 0.14456 | 0.00049706 | 0.0005681 |
| 0.09008 | 0.0013596 | 0.00070078 | 0.11736 | 3.66E-07 | 0.00047994 | 0.14562 | 0.0001867 | 0.00041546 |
| 0.09123 | 0.00015981 | 0.00038324 | 0.11831 | 1.75E-11 | 0.00010207 | 0.14651 | 0.00034975 | 0.00060545 |
| 0.09204 | 0.00023162 | 0.00050758 | 0.11934 | 4.38E-07 | 0.00055093 | 0.14827 | 0.0026817 | 0.00080273 |
| 0.09294 | 1.56E-05 | 0.00025853 | 0.12028 | 3.88E-07 | 0.00036829 | 0.14988 | 0.00036166 | 0.00047435 |
| 0.09381 | 0.00065234 | 0.00061904 | 0.12109 | 1.37E-06 | 0.00051394 | 0.15112 | 0.0030896 | 0.00073611 |
| 0.09487 | 3.93E-05 | 0.00030967 | 0.12191 | 7.35E-08 | 0.00020397 | 0.15274 | 0.0019005 | 0.00079475 |
| 0.09561 | 0.00014074 | 0.00047449 | 0.12298 | 3.38E-05 | 0.0008569 | 0.15373 | 0.00033455 | 0.00040922 |
| 0.09654 | 4.59E-05 | 0.000036141 | 0.12453 | 2.60E-05 | 0.00060909 | 0.15472 | 0.00068466 | 0.00049067 |
| 0.09755 | 0.00068825 | 0.00081709 | 0.12579 | 6.30E-05 | 0.00069643 | 0.15544 | 4.87E-05 | 0.00023768 |
| 0.09914 | 0.00059198 | 0.0007032 | 0.12738 | 0.00010915 | 0.00080518 | 0.15647 | 0.0023925 | 0.00062638 |
| 0.1004 | 0.00022571 | 0.00059337 | 0.12838 | 5.47E-06 | 0.00033937 | 0.15737 | 0.00018098 | 0.00033902 |
| 0.10198 | 0.00055453 | 0.00082877 | 0.12929 | 2.37E-05 | 0.0004738 | 0.15829 | 0.00075426 | 0.00048059 |
| 0.10301 | 2.27E-07 | 0.00012542 | 0.13004 | 9.21E-06 | 0.00032766 | 0.15905 | 0.00031809 | 0.00032485 |
| 0.10384 | 5.17E-05 | 0.00052328 | 0.13111 | 0.00012773 | 0.00061408 | 0.16021 | 0.0070097 | 0.00073795 |
| 0.10466 | 2.87E-05 | 0.00038784 | 0.13197 | 2.06E-06 | 0.00023097 | 0.16178 | 0.00641 | 0.00079859 |
| 0.10572 | 0.00011614 | 0.00059549 | 0.13286 | 5.39E-05 | 0.00051803 | 0.16297 | 0.0041308 | 0.00082719 |
| 0.10654 | 5.16E-08 | 9.60E-05 | 0.13369 | 3.97E-05 | 0.00039522 | 0.16451 | 0.015263 | 0.00076215 |
| 0.10743 | 4.71E-05 | 0.00058193 | 0.13483 | 0.00028317 | 0.00068676 | 0.16565 | 0.00013234 | 0.00021109 |
| 0.10832 | 2.07E-05 | 0.00042372 | 0.13645 | 0.00059495 | 0.00079679 | 0.16634 | 0.0024543 | 0.000488 |
| 0.1094 | 4.74E-05 | 0.00060145 | 0.1376 | 6.80E-05 | 0.00066745 | 0.16731 | 0.0014238 | 0.00039467 |
| 0.11107 | 0.00010881 | 0.00080903 | 0.13917 | 0.0010224 | 0.00078555 | 0.16824 | 0.010167 | 0.00063399 |
| 0.11218 | 9.69E-09 | 0.00012002 | 0.14091 | 0.00022002 | 0.00054068 | 0.16921 | 3.79E-05 | 0.00014279 |
| 0.11271 | 3.37E-07 | 0.00031694 | 0.14195 | 0.0001209 | 0.00042554 | 0.16995 | 0.0078375 | 0.00052665 |

FIG. 9

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.17098 | 0.004942 | 0.00042415 | 0.19732 | 0.0074259 | 0.0008003 | 0.22815 | 5.36E-06 | 0.00024362 |
| 0.17195 | 0.01847 | 0.0007608 | 0.19893 | 0.010374 | 0.00073033 | 0.22901 | 7.51E-05 | 0.00049625 |
| 0.17363 | 0.10166 | 0.00077222 | 0.20018 | 0.0015942 | 0.00050401 | 0.2298 | 3.83E-05 | 0.00036797 |
| 0.17479 | 0.0016992 | 0.0002637 | 0.20178 | 0.0090259 | 0.00080833 | 0.23087 | 0.00022268 | 0.00060592 |
| 0.17528 | 0.00071578 | 0.00020127 | 0.20356 | 0.0010909 | 0.00058508 | 0.23171 | 5.58E-07 | 0.00014967 |
| 0.1765 | 0.29643 | 0.00076383 | 0.20443 | 0.00061322 | 0.00041123 | 0.23259 | 8.05E-05 | 0.00055897 |
| 0.17818 | 0.18527 | 0.00066067 | 0.2055 | 0.0017976 | 0.00057422 | 0.23346 | 4.39E-05 | 0.00041681 |
| 0.17908 | 0.10571 | 0.000041795 | 0.20628 | 1.23E-10 | 1.12E-05 | 0.23457 | 0.00014327 | 0.00063487 |
| 0.17987 | 0.041737 | 0.00033099 | 0.2072 | 0.0012666 | 0.000060577 | 0.23621 | 0.0003103 | 0.00080968 |
| 0.18043 | 0.013217 | 0.000025312 | 0.20811 | 0.00044799 | 0.000042713 | 0.23734 | 3.76E-06 | 0.00040116 |
| 0.18086 | 0.00049725 | 0.000012223 | 0.20916 | 0.00087738 | 0.0005529 | 0.23893 | 0.00022461 | 0.00078351 |
| 0.18179 | 0.29741 | 0.00063219 | 0.21089 | 0.0038931 | 0.00078809 | 0.24063 | 4.36E-05 | 0.00059138 |
| 0.18273 | 0.033345 | 0.000039804 | 0.21246 | 0.0001928 | 0.00060686 | 0.24171 | 1.35E-05 | 0.00042858 |
| 0.18371 | 0.038699 | 0.00049574 | 0.2136 | 0.0025903 | 0.00079942 | 0.2426 | 2.33E-05 | 0.00057666 |
| 0.18441 | 0.00078141 | 0.0001763 | 0.21523 | 0.0011748 | 0.00067427 | 0.24352 | 5.79E-09 | 7.32E-05 |
| 0.18552 | 0.14671 | 0.00077029 | 0.21636 | 0.00020186 | 0.00040245 | 0.24431 | 2.60E-05 | 0.00058562 |
| 0.18707 | 0.025246 | 0.0008724 | 0.2172 | 0.00028837 | 0.00052834 | 0.24539 | 4.58E-06 | 0.00039652 |
| 0.18826 | 0.04249 | 0.00078683 | 0.2181 | 7.63E-06 | 0.00021039 | 0.24621 | 5.61E-06 | 0.00052371 |
| 0.18984 | 0.034479 | 0.000073443 | 0.21895 | 0.00072242 | 0.000061309 | 0.248 | 2.35E-05 | 0.00078072 |
| 0.19101 | 0.0017993 | 0.000033974 | 0.22002 | 6.74E-05 | 0.00033937 | 0.24961 | 2.85E-06 | 0.0006045 |
| 0.19177 | 0.0034381 | 0.000048311 | 0.22078 | 0.00015827 | 0.00047752 | 0.25081 | 3.05E-06 | 0.00067001 |
| 0.19269 | 0.00063811 | 0.0003246 | 0.22168 | 3.15E-05 | 0.000031943 | 0.25203 | 2.34E-07 | 0.00066694 |
| 0.19358 | 0.0099082 | 0.000062442 | 0.22269 | 0.00098977 | 0.00082192 | 0.25303 | 1.65E-09 | 0.00016979 |
| 0.19462 | 0.0002517 | 0.000025404 | 0.22428 | 0.00064413 | 0.00067951 | 0.25359 | 2.20E-08 | 0.0003599 |
| 0.19534 | 0.0024547 | 0.000048539 | 0.22554 | 0.00042852 | 0.00063577 | 0.2545 | 2.92E-07 | 0.00045313 |
| 0.19632 | 0.0011258 | 0.000040253 | 0.22712 | 0.00074722 | 0.00083499 | 0.25521 | 1.25E-07 | 0.000029555 |

FIG. 10

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.25628 | 4.74E-06 | 0.00060516 | 0.28534 | 0.0011572 | 0.00074952 | 0.31615 | 0.0012063 | 0.00036871 |
| 0.25713 | 2.14E-07 | 0.00027797 | 0.2869 | 0.00069393 | 0.00079992 | 0.31695 | 0.002262 | 0.00050168 |
| 0.25804 | 3.05E-06 | 0.00049353 | 0.28809 | 0.00072758 | 0.00082394 | 0.31785 | 0.00029533 | 0.0002836 |
| 0.25883 | 2.45E-06 | 0.00037357 | 0.28964 | 0.0016468 | 0.00075044 | 0.31874 | 0.010407 | 0.0006278 |
| 0.25999 | 3.10E-05 | 0.00071372 | 0.29079 | 4.09E-05 | 0.00027311 | 0.31978 | 0.00061788 | 0.00028998 |
| 0.26159 | 5.84E-05 | 0.00078718 | 0.29151 | 0.00023018 | 0.00048027 | 0.32052 | 0.0037247 | 0.00047939 |
| 0.26275 | 1.59E-05 | 0.00078938 | 0.29245 | 0.0001004 | 0.00037284 | 0.32146 | 0.0018815 | 0.00037733 |
| 0.26431 | 0.00013862 | 0.00077785 | 0.29338 | 0.00094854 | 0.00063249 | 0.3225 | 0.027004 | 0.00085321 |
| 0.26608 | 2.72E-05 | 0.00051502 | 0.29437 | 9.37E-06 | 0.0001885 | 0.32409 | 0.045221 | 0.00070659 |
| 0.26709 | 1.68E-05 | 0.00041791 | 0.2951 | 0.00047635 | 0.00050918 | 0.32534 | 0.019049 | 0.00057849 |
| 0.26801 | 7.15E-05 | 0.00062302 | 0.29611 | 0.00028086 | 0.00042062 | 0.32695 | 0.1106 | 0.00079615 |
| 0.26895 | 1.16E-08 | 6.46E-05 | 0.2971 | 0.0012371 | 0.00078409 | 0.32876 | 0.023841 | 0.00052979 |
| 0.26971 | 7.48E-05 | 0.00055249 | 0.29874 | 0.0037579 | 0.00075274 | 0.32959 | 0.020504 | 0.0003999 |
| 0.27076 | 3.46E-05 | 0.00042258 | 0.29995 | 0.00019801 | 0.00037617 | 0.33068 | 0.13074 | 0.00058245 |
| 0.27168 | 7.79E-05 | 0.0006591 | 0.30159 | 0.0050566 | 0.00078114 | 0.33144 | 2.05E-05 | 6.45E-05 |
| 0.2734 | 0.00049037 | 0.00078968 | 0.3033 | 0.0011593 | 0.00065446 | 0.33238 | 0.18537 | 0.00056829 |
| 0.27503 | 3.05E-05 | 0.000039048 | 0.30422 | 0.00059693 | 0.00042495 | 0.33324 | 0.10369 | 0.00041231 |
| 0.27625 | 0.00060264 | 0.000074961 | 0.30527 | 0.0015577 | 0.00054849 | 0.334 | 0.02316 | 0.00030249 |
| 0.27789 | 0.0002753 | 0.00076841 | 0.30601 | 4.79E-07 | 7.35E-05 | 0.33464 | 0.03299 | 0.00044784 |
| 0.27887 | 6.95E-05 | 0.00042087 | 0.30697 | 0.0022537 | 0.00061675 | 0.33598 | 1 | 0.00078609 |
| 0.27987 | 0.00013849 | 0.00050541 | 0.30789 | 0.00062572 | 0.00041846 | 0.3376 | 0.0083042 | 0.00045244 |
| 0.28059 | 3.70E-06 | 0.00019594 | 0.3089 | 0.0012852 | 0.00051013 | 0.3387 | 0.2716 | 0.00077559 |
| 0.28161 | 0.00037913 | 0.00062756 | 0.3107 | 0.010683 | 0.00077133 | 0.34037 | 0.059762 | 0.00064927 |
| 0.28252 | 4.35E-05 | 0.00036951 | 0.31224 | 0.0021122 | 0.00073213 | 0.34149 | 0.011093 | 0.00041723 |
| 0.28346 | 0.00012132 | 0.00047814 | 0.31342 | 0.010098 | 0.00082498 | 0.34235 | 0.01451 | 0.00054543 |
| 0.28419 | 2.76E-05 | 0.00028178 | 0.31501 | 0.010071 | 0.00070846 | 0.34326 | 9.53E-05 | 0.00015878 |

FIG. 11

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.34408 | 0.023398 | 0.00060314 | 0.37317 | 0.0021809 | 0.00079867 | 0.40125 | 5.30E-06 | 0.00074817 |
| 0.34516 | 0.0027549 | 0.00036498 | 0.37478 | 0.00030648 | 0.00052123 | 0.40335 | 3.11E-08 | 0.00030639 |
| 0.34594 | 0.004472 | 0.00048819 | 0.37602 | 0.0013752 | 0.00072404 | 0.40407 | 1.86E-07 | 0.00041849 |
| 0.34682 | 0.00031852 | 0.00025787 | 0.37763 | 0.00072781 | 0.00083352 | 0.40508 | 1.44E-06 | 0.00050696 |
| 0.34782 | 0.026774 | 0.00081294 | 0.37864 | 8.13E-05 | 0.00039716 | 0.40576 | 1.88E-08 | 0.00015071 |
| 0.34941 | 0.011101 | 0.00065283 | 0.37961 | 0.0001436 | 0.00048552 | 0.40678 | 9.17E-06 | 0.00060634 |
| 0.35068 | 0.011449 | 0.00066598 | 0.38034 | 1.40E-05 | 0.0002601 | 0.40768 | 2.21E-06 | 0.00039572 |
| 0.35225 | 0.013158 | 0.00084533 | 0.38137 | 0.00038192 | 0.00063065 | 0.40864 | 6.70E-06 | 0.00048035 |
| 0.35329 | 0.00029157 | 0.00030959 | 0.38227 | 1.77E-05 | 0.00031694 | 0.40933 | 6.54E-07 | 0.00022308 |
| 0.35418 | 0.0013765 | 0.0004818 | 0.38318 | 8.06E-05 | 0.00048938 | 0.4105 | 9.93E-05 | 0.00075764 |
| 0.35495 | 0.00053258 | 0.00034349 | 0.38396 | 3.55E-05 | 0.00034478 | 0.41205 | 5.29E-05 | 0.00076247 |
| 0.35601 | 0.0043421 | 0.0006153 | 0.3851 | 0.00043235 | 0.0007239 | 0.41323 | 0.00011358 | 0.00084486 |
| 0.35687 | 3.33E-05 | 0.00020157 | 0.38667 | 0.00032312 | 0.00083135 | 0.41479 | 0.00021728 | 0.00073511 |
| 0.35775 | 0.0012769 | 0.000053673 | 0.38786 | 0.00010858 | 0.000075935 | 0.41593 | 1.25E-05 | 0.00031804 |
| 0.3586 | 0.00075849 | 0.00040421 | 0.3894 | 0.00033441 | 0.000076428 | 0.41668 | 3.98E-05 | 0.000048317 |
| 0.35972 | 0.0033858 | 0.00066538 | 0.39056 | 6.41E-07 | 0.000015991 | 0.4176 | 1.32E-05 | 0.00034292 |
| 0.36135 | 0.0058036 | 0.000081419 | 0.39123 | 3.17E-05 | 0.000049303 | 0.41852 | 0.00020561 | 0.0006337 |
| 0.3625 | 0.00029458 | 0.00056707 | 0.39221 | 1.39E-05 | 0.000040817 | 0.41953 | 4.84E-06 | 0.0002307 |
| 0.36407 | 0.0052252 | 0.00078189 | 0.39313 | 5.81E-05 | 0.00061756 | 0.42026 | 9.44E-05 | 0.00049473 |
| 0.3658 | 0.0008927 | 0.00055828 | 0.39411 | 6.25E-08 | 0.00011494 | 0.42125 | 5.91E-05 | 0.00040935 |
| 0.36685 | 0.00036651 | 0.00042914 | 0.39484 | 2.55E-05 | 0.00053296 | 0.42226 | 0.0003979 | 0.00082329 |
| 0.36776 | 0.00084439 | 0.000059684 | 0.39588 | 9.15E-06 | 0.00042836 | 0.42387 | 0.00098658 | 0.00073663 |
| 0.36869 | 9.09E-10 | 1.96E-05 | 0.39681 | 1.76E-05 | 0.000067348 | 0.4251 | 0.00013475 | 0.00046582 |
| 0.36946 | 0.00091264 | 0.00057494 | 0.39847 | 3.82E-05 | 0.00075836 | 0.42673 | 0.0016057 | 0.00078991 |
| 0.37053 | 0.00024501 | 0.00041029 | 0.39969 | 4.34E-08 | 0.00017112 | 0.42847 | 0.00031884 | 0.00060264 |
| 0.37139 | 0.00036383 | 0.00056949 | 0.40017 | 2.31E-07 | 0.00028567 | 0.42936 | 0.00020213 | 0.00041839 |

FIG. 12

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.43042 | 0.0006582 | 0.0005639 | 0.45752 | 0.18868 | 0.00049278 | 0.48487 | 0.00078675 | 0.00069058 |
| 0.43118 | 1.22E-09 | 2.15E-05 | 0.45836 | 0.068215 | 0.00041542 | 0.48647 | 0.00093231 | 0.00082508 |
| 0.43212 | 0.00077456 | 0.00060566 | 0.45944 | 0.09935 | 0.00061268 | 0.48764 | 0.00010804 | 0.00067085 |
| 0.43303 | 0.00028876 | 0.00042682 | 0.4611 | 0.12803 | 0.00082952 | 0.48919 | 0.00078032 | 0.00077346 |
| 0.43407 | 0.00065478 | 0.000053563 | 0.46225 | 0.00024328 | 0.00026784 | 0.49096 | 9.29E-05 | 0.00052834 |
| 0.43583 | 0.0047647 | 0.00077658 | 0.46278 | 5.57E-05 | 0.000019436 | 0.49199 | 3.91E-05 | 0.00042584 |
| 0.43739 | 0.00052643 | 0.00065234 | 0.46384 | 0.049033 | 0.00077967 | 0.4929 | 0.00010332 | 0.00060465 |
| 0.43855 | 0.0053858 | 0.00082233 | 0.46553 | 0.0093708 | 0.00061294 | 0.49385 | 9.79E-10 | 3.44E-05 |
| 0.44016 | 0.0041578 | 0.00068476 | 0.46663 | 0.0024146 | 0.0004259 | 0.4946 | 6.84E-05 | 0.00055863 |
| 0.44129 | 0.00075924 | 0.00039103 | 0.46751 | 0.0037128 | 0.00056649 | 0.49566 | 1.89E-05 | 0.00042112 |
| 0.44212 | 0.0013264 | 0.00052153 | 0.46842 | 4.24E-06 | 0.000010503 | 0.49655 | 2.66E-05 | 0.00060302 |
| 0.443 | 7.85E-05 | 0.00023843 | 0.46922 | 0.0050279 | 0.0005936 | 0.49827 | 8.47E-05 | 0.00077067 |
| 0.44388 | 0.0056678 | 0.00062233 | 0.4703 | 0.00082124 | 0.00038606 | 0.49991 | 3.21E-06 | 0.000045182 |
| 0.44493 | 0.0005522 | 0.00032206 | 0.47111 | 0.001151 | 0.000051073 | 0.50107 | 1.35E-05 | 0.000072051 |
| 0.44569 | 0.0020251 | 0.00047828 | 0.47196 | 8.99E-06 | 0.000015359 | 0.50236 | 5.84E-07 | 0.00063959 |
| 0.4466 | 0.00073509 | 0.00034369 | 0.47295 | 0.0070954 | 0.0008077 | 0.50332 | 6.88E-10 | 0.0001034 |
| 0.44765 | 0.020289 | 0.000086194 | 0.47455 | 0.0019757 | 0.000061347 | 0.50389 | 9.74E-08 | 0.000038521 |
| 0.44923 | 0.027231 | 0.00068203 | 0.47581 | 0.0033659 | 0.000069104 | 0.50483 | 1.18E-06 | 0.00047458 |
| 0.45049 | 0.021781 | 0.000063442 | 0.47739 | 0.0027243 | 0.00084974 | 0.50551 | 1.12E-07 | 0.00022054 |
| 0.4521 | 0.097925 | 0.000079185 | 0.47842 | 0.00012587 | 0.00035368 | 0.50656 | 1.40E-05 | 0.00060676 |
| 0.45307 | 0.00037235 | 0.00018693 | 0.47935 | 0.00032714 | 0.00047728 | 0.50744 | 1.89E-06 | 0.0003543 |
| 0.45394 | 0.029148 | 0.000049504 | 0.4801 | 8.24E-05 | 0.0003146 | 0.50837 | 8.96E-06 | 0.00047352 |
| 0.45474 | 0.03004 | 0.00038247 | 0.48114 | 0.00097874 | 0.00062326 | 0.50911 | 3.71E-06 | 0.00030825 |
| 0.45582 | 0.35649 | 0.00056749 | 0.48203 | 1.67E-05 | 0.00025009 | 0.51028 | 0.00013441 | 0.00074466 |
| 0.45659 | 0.0001188 | 0.00010692 | 0.48291 | 0.00022958 | 0.00051608 | 0.51184 | 0.0001341 | 0.00077959 |
| 0.45677 | 5.43E-06 | 5.09E-05 | 0.48374 | 0.00013099 | 0.00038611 | 0.51303 | 0.00012326 | 0.00084968 |

FIG. 13

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.51457 | 0.00042892 | 0.00075668 | 0.54186 | 0.0064432 | 0.00049655 | 0.57007 | 0.0001281 | 0.00035056 |
| 0.5157 | 6.76E-06 | 0.00023957 | 0.54276 | 0.0015514 | 0.00030594 | 0.57084 | 0.00025256 | 0.00048063 |
| 0.51641 | 7.30E-05 | 0.0004841 | 0.54369 | 0.051885 | 0.00064018 | 0.57173 | 3.49E-05 | 0.000029695 |
| 0.51737 | 4.00E-05 | 0.00038592 | 0.5447 | 0.0034385 | 0.00026867 | 0.57274 | 0.0015298 | 0.00081646 |
| 0.5183 | 0.00032861 | 0.00063419 | 0.54545 | 0.045367 | 0.00048862 | 0.57433 | 0.00080218 | 0.00067036 |
| 0.51928 | 1.97E-06 | 0.000016202 | 0.5464 | 0.049056 | 0.0003823 | 0.57559 | 0.00061925 | 0.00064787 |
| 0.52001 | 0.00021727 | 0.00051913 | 0.54718 | 0.34018 | 0.00040612 | 0.57717 | 0.0008578 | 0.00084303 |
| 0.52103 | 0.00013359 | 0.00042336 | 0.54801 | 0.16181 | 0.0004387 | 0.57821 | 1.02E-05 | 0.00027456 |
| 0.52201 | 0.00052173 | 0.00076823 | 0.54891 | 0.58019 | 0.00073387 | 0.57908 | 8.00E-05 | 0.00048971 |
| 0.52366 | 0.0020841 | 0.00076204 | 0.55021 | 0.050391 | 0.00051725 | 0.57986 | 3.56E-05 | 0.00035813 |
| 0.52485 | 5.74E-05 | 0.00031443 | 0.55178 | 0.11316 | 0.00083896 | 0.58092 | 0.00022264 | 0.00061074 |
| 0.52534 | 1.19E-06 | 0.00011539 | 0.55362 | 0.0076901 | 0.000057513 | 0.58177 | 8.81E-07 | 0.00017151 |
| 0.52652 | 0.003249 | 0.0007727 | 0.55448 | 0.0037272 | 0.00040516 | 0.58265 | 6.54E-05 | 0.0005516 |
| 0.52821 | 0.00095213 | 0.0006786 | 0.55554 | 0.0099411 | 0.00058173 | 0.58351 | 3.47E-05 | 0.00041164 |
| 0.52914 | 0.00045577 | 0.00042735 | 0.55634 | 6.12E-08 | 3.36E-05 | 0.58462 | 0.0001157 | 0.00064567 |
| 0.53019 | 0.0011631 | 0.00053836 | 0.55725 | 0.0049318 | 0.00060418 | 0.58625 | 0.00018832 | 0.0008206 |
| 0.53092 | 1.63E-06 | 0.00010259 | 0.55816 | 0.0017168 | 0.00042673 | 0.5874 | 3.87E-06 | 0.00046931 |
| 0.53189 | 0.0021999 | 0.00061842 | 0.55922 | 0.0032084 | 0.00056548 | 0.58896 | 9.32E-05 | 0.00076966 |
| 0.53281 | 0.00054912 | 0.00041172 | 0.56093 | 0.011099 | 0.00079519 | 0.59068 | 1.05E-05 | 0.00057675 |
| 0.5338 | 0.0012198 | 0.00049771 | 0.56252 | 0.00032285 | 0.0005482 | 0.59175 | 2.32E-06 | 0.0004308 |
| 0.53447 | 1.08E-05 | 0.00013123 | 0.56365 | 0.0063015 | 0.00079283 | 0.59262 | 2.56E-06 | 0.00054927 |
| 0.53562 | 0.012856 | 0.0007664 | 0.56529 | 0.0022912 | 0.00066345 | 0.59359 | 5.19E-11 | 5.09E-05 |
| 0.53717 | 0.004014 | 0.00074116 | 0.56642 | 0.00042184 | 0.00040903 | 0.59419 | 2.14E-07 | 0.0004514 |
| 0.53836 | 0.015278 | 0.00084481 | 0.56726 | 0.00058477 | 0.0005359 | 0.59491 | 8.20E-10 | 0.00013356 |
| 0.53994 | 0.022885 | 0.00071784 | 0.56816 | 9.16E-06 | 0.00018922 | 0.59553 | 1.04E-07 | 0.00035546 |
| 0.54107 | 0.0025735 | 0.00035213 | 0.569 | 0.0012407 | 0.00060902 | 0.59637 | 7.74E-07 | 0.00057121 |

FIG. 14

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.59818 | 2.77E-05 | 0.00083907 | 0.62795 | 0.0017637 | 0.00075173 | 0.65532 | 0.26897 | 0.00054029 |
| 0.59972 | 1.34E-05 | 0.00054021 | 0.62892 | 0.00052155 | 0.00042402 | 0.65608 | 1.36E-05 | 5.15E-05 |
| 0.60098 | 7.47E-05 | 0.00072204 | 0.62994 | 0.0010837 | 0.0005119 | 0.65699 | 0.14131 | 0.00063352 |
| 0.60258 | 8.78E-05 | 0.000079214 | 0.63066 | 1.83E-05 | 0.00017748 | 0.65793 | 0.026516 | 0.00041746 |
| 0.60357 | 1.05E-05 | 0.00038685 | 0.63166 | 0.0028318 | 0.00062617 | 0.65895 | 0.033976 | 0.00052207 |
| 0.60453 | 2.81E-05 | 0.00047713 | 0.63258 | 0.00039428 | 0.0003806 | 0.66071 | 0.1277 | 0.0007848 |
| 0.60525 | 5.16E-06 | 0.00028177 | 0.63353 | 0.0010229 | 0.00047908 | 0.66227 | 0.011517 | 0.00078083 |
| 0.60631 | 0.00013914 | 0.00062088 | 0.63424 | 0.00016793 | 0.00025972 | 0.66344 | 0.050341 | 0.0007922 |
| 0.60719 | 6.03E-06 | 0.00029506 | 0.6354 | 0.010735 | 0.00075428 | 0.66505 | 0.027485 | 0.00070706 |
| 0.60809 | 5.06E-05 | 0.0004925 | 0.63696 | 0.0059855 | 0.00078755 | 0.6662 | 0.0028274 | 0.0003796 |
| 0.60888 | 3.21E-05 | 0.00036259 | 0.63815 | 0.0084711 | 0.00083697 | 0.667 | 0.0040156 | 0.00050378 |
| 0.61004 | 0.00040428 | 0.00071917 | 0.63971 | 0.018451 | 0.00074481 | 0.6679 | 0.00030043 | 0.00026633 |
| 0.61163 | 0.00055676 | 0.00079841 | 0.64084 | 0.00070366 | 0.00029348 | 0.66878 | 0.010928 | 0.00061966 |
| 0.6128 | 0.00018026 | 0.000079304 | 0.64158 | 0.0031186 | 0.00048121 | 0.66984 | 0.00059833 | 0.00030432 |
| 0.61435 | 0.0011302 | 0.00077321 | 0.64252 | 0.0013213 | 0.00036063 | 0.67057 | 0.0023306 | 0.00047496 |
| 0.61547 | 1.43E-07 | 7.55E-05 | 0.64344 | 0.01647 | 0.000063635 | 0.67151 | 0.00080643 | 0.00036704 |
| 0.61614 | 0.00019216 | 0.00050594 | 0.64444 | 0.00026581 | 0.00020632 | 0.67252 | 0.011014 | 0.00008181 |
| 0.61714 | 0.00011537 | 0.00041357 | 0.64517 | 0.0096037 | 0.00050388 | 0.67411 | 0.010278 | 0.00070598 |
| 0.61807 | 0.00053773 | 0.00062557 | 0.64617 | 0.0067662 | 0.00041519 | 0.67538 | 0.0037193 | 0.00058699 |
| 0.61902 | 2.58E-07 | 8.57E-05 | 0.64718 | 0.041939 | 0.00083341 | 0.67696 | 0.010519 | 0.00082362 |
| 0.61977 | 0.0004871 | 0.00054567 | 0.64882 | 0.1685 | 0.00074799 | 0.67798 | 1.08E-06 | 8.81E-05 |
| 0.62081 | 0.00023783 | 0.00042449 | 0.65002 | 0.019611 | 0.00042012 | 0.6788 | 0.0011036 | 0.00052717 |
| 0.62174 | 0.0005813 | 0.00068166 | 0.65169 | 0.67361 | 0.00076674 | 0.67963 | 0.00065654 | 0.00039117 |
| 0.62345 | 0.0032987 | 0.00078424 | 0.65328 | 0.16756 | 0.00060364 | 0.6807 | 0.0027752 | 0.0005928 |
| 0.62509 | 0.00013448 | 0.00034965 | 0.65397 | 0.00030685 | 9.25E-05 | 0.68151 | 9.17E-07 | 8.66E-05 |
| 0.62631 | 0.0042298 | 0.00075499 | 0.65442 | 0.025865 | 0.00031572 | 0.68241 | 0.0014015 | 0.00058183 |

FIG. 15

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.6833 | 0.00066988 | 0.00042571 | 0.71256 | 8.35E-05 | 0.00062416 | 0.74319 | 5.25E-05 | 0.00062427 |
| 0.68438 | 0.0017293 | 0.000598 | 0.71412 | 0.0010907 | 0.00078083 | 0.74418 | 1.20E-07 | 0.00013468 |
| 0.68607 | 0.005619 | 0.00079768 | 0.71587 | 0.00018077 | 0.0005456 | 0.74491 | 2.62E-05 | 0.0005275 |
| 0.68768 | 4.01E-05 | 0.00035345 | 0.71691 | 8.18E-05 | 0.00042772 | 0.74594 | 1.18E-05 | 0.0004272 |
| 0.68878 | 0.0044873 | 0.00079483 | 0.71782 | 0.00021398 | 0.00060375 | 0.74689 | 3.07E-05 | 0.00071381 |
| 0.69045 | 0.0014076 | 0.00063 | 0.71952 | 0.00022006 | 0.00056935 | 0.74856 | 9.47E-05 | 0.00076584 |
| 0.69155 | 0.00037608 | 0.00042038 | 0.72059 | 6.72E-05 | 0.0004148 | 0.74975 | 6.58E-07 | 0.00023961 |
| 0.69243 | 0.00060818 | 0.0005592 | 0.72146 | 0.00010692 | 0.00058965 | 0.75024 | 5.13E-07 | 0.00022826 |
| 0.69332 | 2.41E-06 | 0.00013661 | 0.72323 | 0.00063602 | 0.00079645 | 0.75141 | 6.82E-05 | 0.00077134 |
| 0.69415 | 0.0011829 | 0.00060123 | 0.72484 | 7.37E-05 | 0.0004906 | 0.75309 | 1.46E-05 | 0.00073395 |
| 0.69522 | 0.00018419 | 0.0003739 | 0.72608 | 0.00045621 | 0.00073169 | 0.75404 | 4.58E-06 | 0.00042518 |
| 0.69602 | 0.00030371 | 0.000049851 | 0.72769 | 0.00022608 | 0.0008209 | 0.75508 | 7.93E-06 | 0.00053025 |
| 0.69687 | 1.25E-05 | 0.00022215 | 0.7287 | 3.14E-05 | 0.00040503 | 0.75582 | 2.65E-08 | 0.00013092 |
| 0.69788 | 0.0022604 | 0.00081919 | 0.72968 | 5.51E-05 | 0.00048995 | 0.75678 | 1.00E-05 | 0.00063256 |
| 0.69947 | 0.00092399 | 0.00063349 | 0.7304 | 3.99E-06 | 0.00024419 | 0.75771 | 1.51E-06 | 0.00039883 |
| 0.70073 | 0.0013002 | 0.00067989 | 0.73143 | 0.00014688 | 0.00063087 | 0.75869 | 2.41E-06 | 0.00049106 |
| 0.70232 | 0.0014542 | 0.00083885 | 0.73234 | 8.73E-06 | 0.00033223 | 0.75938 | 8.10E-08 | 0.0001912 |
| 0.70334 | 4.86E-05 | 0.00033048 | 0.73325 | 3.34E-05 | 0.00048444 | 0.7605 | 1.26E-05 | 0.00076403 |
| 0.70425 | 0.0001829 | 0.00047791 | 0.73401 | 1.32E-05 | 0.00033083 | 0.76203 | 2.40E-06 | 0.000088252 |
| 0.70501 | 6.35E-05 | 0.00033212 | 0.73516 | 0.00021211 | 0.00073192 | 0.76321 | 3.22E-06 | 0.00076158 |
| 0.70607 | 0.00064327 | 0.00061763 | 0.73673 | 0.00015112 | 0.00082476 | 0.76477 | 1.80E-06 | 0.00074053 |
| 0.70693 | 7.47E-06 | 0.0002224 | 0.73792 | 6.95E-05 | 0.00078211 | 0.76596 | 4.48E-08 | 0.00033189 |
| 0.70782 | 0.00019154 | 0.000052645 | 0.73946 | 0.00019836 | 0.00076217 | 0.76668 | 4.42E-08 | 0.00044795 |
| 0.70866 | 0.00011929 | 0.000039765 | 0.74061 | 1.01E-06 | 0.00019793 | 0.76757 | 1.24E-09 | 0.00030333 |
| 0.70978 | 0.0006422 | 0.0006778 | 0.7413 | 2.12E-05 | 0.00048781 | 0.76802 | 9.55E-12 | 7.82E-05 |
| 0.7114 | 0.0010462 | 0.00081293 | 0.74227 | 9.87E-06 | 0.00040018 | 0.7688 | 3.28E-08 | 0.00055588 |

FIG. 16

Class R waveform

| time (sec) | local peak amplitude (normalized to waveform peak) | half-height interval (sec) |
|---|---|---|
| 0.76961 | 5.57E-09 | 0.00024375 |
| 0.77036 | 1.52E-07 | 0.00048884 |
| 0.77132 | 1.66E-07 | 0.0003964 |
| 0.77236 | 2.02E-06 | 0.0008844 |
| 0.77394 | 6.84E-06 | 0.000725 |
| 0.77516 | 1.59E-06 | 0.00050182 |
| 0.77679 | 1.81E-05 | 0.00078663 |
| 0.77855 | 3.93E-06 | 0.00057952 |
| 0.77941 | 2.79E-06 | 0.00041451 |
| 0.78048 | 1.05E-05 | 0.00056936 |
| 0.78218 | 1.18E-05 | 0.000059924 |
| 0.78309 | 4.99E-06 | 0.00042863 |
| 0.78414 | 1.21E-05 | 0.00054776 |
| 0.78588 | 8.07E-05 | 0.000077871 |
| 0.78744 | 6.35E-06 | 0.00060889 |
| 0.7886 | 9.08E-05 | 0.00081661 |
| 0.79022 | 5.86E-05 | 0.0006746 |
| 0.79134 | 1.17E-05 | 0.0003988 |
| 0.79218 | 1.94E-05 | 0.00052894 |
| 0.79307 | 7.17E-07 | 0.00021856 |
| 0.79393 | 6.80E-05 | 0.00061749 |
| 0.79499 | 7.13E-06 | 0.00033428 |
| 0.79575 | 2.03E-05 | 0.00047866 |
| 0.79665 | 5.26E-06 | 0.00032658 |
| 0.79768 | 0.00017128 | 0.000084091 |
| 0.79926 | 0.00015373 | 0.00067708 |
| 0.80053 | 0.00011604 | 0.00063722 |
| 0.80211 | 0.00028115 | 0.00081857 |
| 0.80312 | 1.81E-06 | 0.00022956 |
| 0.80398 | 3.86E-05 | 0.0004966 |
| 0.80478 | 2.32E-05 | 0.00037225 |
| 0.80585 | 0.00015384 | 0.00060188 |
| 0.80667 | 3.53E-07 | 0.00014094 |
| 0.80757 | 7.82E-05 | 0.00055743 |
| 0.80844 | 4.89E-05 | 0.000041957 |
| 0.80955 | 0.00018663 | 0.00063251 |
| 0.81121 | 0.00057933 | 0.000079539 |
| 0.81232 | 6.19E-06 | 0.00037084 |
| 0.81393 | 0.00071709 | 0.000079654 |
| 0.81561 | 0.00021221 | 0.00059549 |
| 0.81669 | 8.24E-05 | 0.00042625 |
| 0.81759 | 0.00017224 | 0.00058273 |
| 0.81849 | 8.94E-08 | 8.24E-05 |
| 0.8193 | 0.00032359 | 0.00059161 |
| 0.82037 | 7.63E-05 | 0.00039266 |
| 0.82119 | 0.00012526 | 0.000052911 |
| 0.82202 | 3.04E-08 | 6.31E-05 |
| 0.82303 | 0.0011252 | 0.000082022 |
| 0.82462 | 0.00036328 | 0.00058448 |
| 0.82588 | 0.00099583 | 0.000706 |
| 0.82747 | 0.0009664 | 0.00082354 |
| 0.82848 | 7.02E-05 | 0.00036919 |
| 0.82942 | 0.00018711 | 0.00047577 |
| 0.83016 | 4.39E-05 | 0.00030156 |
| 0.83121 | 0.00077141 | 0.00062164 |
| 0.83209 | 2.09E-05 | 0.00026956 |
| 0.83299 | 0.00024274 | 0.00050408 |
| 0.8338 | 0.0001568 | 0.00037751 |
| 0.83494 | 0.0013919 | 0.00070519 |
| 0.83654 | 0.0020283 | 0.00080562 |
| 0.83771 | 0.00041001 | 0.00074106 |
| 0.83926 | 0.0032283 | 0.00077737 |
| 0.84104 | 0.00054426 | 0.00051876 |
| 0.84205 | 0.00030647 | 0.00042036 |
| 0.84298 | 0.0011593 | 0.00061932 |
| 0.84392 | 1.00E-07 | 5.58E-05 |
| 0.84467 | 0.0011374 | 0.00055504 |
| 0.84573 | 0.00048417 | 0.00042207 |
| 0.84664 | 0.0010118 | 0.00064732 |
| 0.84837 | 0.0062207 | 0.00079102 |
| 0.85 | 0.00043151 | 0.00040621 |
| 0.85122 | 0.0070993 | 0.00074764 |
| 0.85286 | 0.0033455 | 0.00077484 |
| 0.85384 | 0.00079474 | 0.00041935 |
| 0.85484 | 0.0015809 | 0.00050275 |
| 0.85556 | 5.08E-05 | 0.00020311 |
| 0.85658 | 0.0045735 | 0.00062725 |
| 0.85749 | 0.00049731 | 0.000365 |

FIG. 17

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.85843 | 0.0014956 | 0.00047772 | 0.88563 | 0.053666 | 0.00077718 | 0.91647 | 5.98E-05 | 0.00041454 |
| 0.85916 | 0.00039305 | 0.00028988 | 0.88719 | 0.0070634 | 0.00081616 | 0.91732 | 8.29E-05 | 0.00054347 |
| 0.86032 | 0.015052 | 0.00074836 | 0.88836 | 0.02121 | 0.00079336 | 0.91822 | 7.25E-07 | 0.00016774 |
| 0.86188 | 0.010322 | 0.000794 | 0.88996 | 0.014071 | 0.00071896 | 0.91905 | 0.00014787 | 0.00060408 |
| 0.86307 | 0.010595 | 0.0008359 | 0.89111 | 0.0011346 | 0.00036491 | 0.92013 | 1.63E-05 | 0.00036094 |
| 0.86462 | 0.028619 | 0.00075261 | 0.8919 | 0.001759 | 0.00049395 | 0.92091 | 2.66E-05 | 0.00048411 |
| 0.86576 | 0.000676 | 0.00026406 | 0.89281 | 0.00020134 | 0.00029169 | 0.92178 | 2.18E-06 | 0.00027047 |
| 0.86648 | 0.0047485 | 0.00048206 | 0.89369 | 0.0050072 | 0.00062198 | 0.92277 | 0.00013138 | 0.00079812 |
| 0.86743 | 0.0024201 | 0.00037603 | 0.89475 | 0.00020384 | 0.00028463 | 0.92436 | 4.33E-05 | 0.0006692 |
| 0.86836 | 0.0243 | 0.00063723 | 0.89547 | 0.0011093 | 0.00047767 | 0.92562 | 2.84E-05 | 0.00064466 |
| 0.86934 | 0.00024054 | 0.00018088 | 0.89643 | 0.0004452 | 0.00038419 | 0.92713 | 1.62E-05 | 0.00090327 |
| 0.87008 | 0.017029 | 0.00051336 | 0.89743 | 0.0043374 | 0.00081104 | 0.92824 | 1.15E-07 | 0.00029 |
| 0.87109 | 0.012439 | 0.00041953 | 0.89903 | 0.0046838 | 0.00071716 | 0.92901 | 1.24E-07 | 0.00044662 |
| 0.8721 | 0.067488 | 0.00082489 | 0.90029 | 0.0011868 | 0.0005553 | 0.92964 | 1.65E-11 | 4.96E-05 |
| 0.87375 | 0.38569 | 0.00076049 | 0.90188 | 0.0042126 | 0.00081918 | 0.93005 | 1.44E-08 | 0.00026914 |
| 0.87493 | 0.029213 | 0.00036203 | 0.9037 | 0.00043879 | 0.00054942 | 0.93108 | 2.41E-06 | 0.00056034 |
| 0.87631 | 0.61958 | 0.00058453 | 0.90454 | 0.00025496 | 0.00040033 | 0.93184 | 4.40E-08 | 0.00019379 |
| 0.87717 | 0.038837 | 0.00041782 | 0.90561 | 0.00088709 | 0.0005858 | 0.93276 | 4.59E-06 | 0.00051648 |
| 0.87823 | 0.21695 | 0.00066694 | 0.90641 | 4.95E-08 | 5.47E-05 | 0.93359 | 4.85E-06 | 0.00040818 |
| 0.87916 | 0.060571 | 0.0004198 | 0.90731 | 0.00048147 | 0.00059381 | 0.93473 | 3.89E-05 | 0.00067041 |
| 0.88021 | 0.079375 | 0.00054964 | 0.90822 | 0.00019767 | 0.00042714 | 0.93637 | 0.00014788 | 0.00077756 |
| 0.88098 | 2.60E-05 | 8.16E-05 | 0.90928 | 0.00042831 | 0.00057861 | 0.93749 | 9.74E-06 | 0.000056972 |
| 0.88191 | 0.049322 | 0.00063493 | 0.91098 | 0.0014599 | 0.00079635 | 0.93908 | 0.00035534 | 0.00079596 |
| 0.88285 | 0.0086653 | 0.00041248 | 0.91258 | 2.66E-05 | 0.00047357 | 0.94078 | 0.00010837 | 0.00056257 |
| 0.88385 | 0.011898 | 0.00050869 | 0.9137 | 0.00091347 | 0.00079132 | 0.94184 | 5.90E-05 | 0.00042663 |
| 0.88453 | 2.09E-06 | 5.45E-05 | 0.91535 | 0.000293 | 0.00065043 | 0.94275 | 0.00016931 | 0.00060374 |

FIG. 18

Class R waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.94365 | 1.15E-09 | 2.85E-05 | 0.97082 | 0.060589 | 0.0004314 | 0.9988 | 0.0002012 | 0.00074047 |
| 0.94445 | 0.00030263 | 0.000057945 | 0.97174 | 0.063258 | 0.00063768 | | | |
| 0.94551 | 0.00010337 | 0.000040674 | 0.97344 | 0.092827 | 0.00076617 | | | |
| 0.94637 | 0.00018916 | 0.00057187 | 0.97466 | 4.52E-05 | 0.00013572 | | | |
| 0.94817 | 0.0018317 | 0.00081538 | 0.97514 | 0.00090394 | 0.00030607 | | | |
| 0.94977 | 0.00042347 | 0.0005248 | 0.97631 | 0.029373 | 0.00076668 | | | |
| 0.95102 | 0.0023462 | 0.000072585 | 0.97798 | 0.0057069 | 0.000078061 | | | |
| 0.95263 | 0.0019736 | 0.00080095 | 0.97896 | 0.0013561 | 0.00042286 | | | |
| 0.95362 | 0.00026633 | 0.00039613 | 0.97998 | 0.0020461 | 0.00052103 | | | |
| 0.95459 | 0.00062521 | 0.0004814 | 0.98072 | 1.59E-05 | 0.00015834 | | | |
| 0.95531 | 8.42E-05 | 0.000026673 | 0.9817 | 0.0027686 | 0.000063563 | | | |
| 0.95636 | 0.0028041 | 0.00062274 | 0.98263 | 0.00033613 | 0.000038753 | | | |
| 0.95725 | 0.00015479 | 0.00031192 | 0.98358 | 0.00059433 | 0.00048499 | | | |
| 0.95816 | 0.001028 | 0.00048639 | 0.98429 | 4.99E-05 | 0.000023452 | | | |
| 0.95894 | 0.00061008 | 0.000035059 | 0.98542 | 0.0035095 | 0.00075826 | | | |
| 0.9601 | 0.01012 | 0.000072972 | 0.98697 | 0.0010238 | 0.00084043 | | | |
| 0.96169 | 0.014449 | 0.00007851 | 0.98816 | 0.0012444 | 0.000079024 | | | |
| 0.96288 | 0.0072495 | 0.000089253 | 0.98973 | 0.0013982 | 0.00074314 | | | |
| 0.96443 | 0.051809 | 0.000077547 | 0.99089 | 4.77E-05 | 0.000031164 | | | |
| 0.96553 | 0.00011617 | 0.00014109 | 0.99163 | 0.00012643 | 0.00047751 | | | |
| 0.96623 | 0.015636 | 0.000050167 | 0.99256 | 3.24E-05 | 0.000035067 | | | |
| 0.96722 | 0.015793 | 0.00040166 | 0.99346 | 0.0003373 | 0.00062353 | | | |
| 0.9682 | 0.17313 | 0.000065513 | 0.9945 | 4.88E-06 | 0.00022406 | | | |
| 0.96908 | 0.00033021 | 0.000010547 | 0.99521 | 8.49E-05 | 0.00049391 | | | |
| 0.96941 | 0.0075215 | 0.00017851 | 0.99621 | 3.67E-05 | 0.00041506 | | | |
| 0.96994 | 0.17093 | 0.000038549 | 0.99718 | 0.00015604 | 0.00076387 | | | |

FIG. 19

Class A waveform

| time (sec) | local peak amplitude (normalized to waveform peak) | half-height interval (sec) |
|---|---|---|
| 0.00123 | 1.22E-12 | 0.00035121 |
| 0.00414 | 0.13263 | 0.00026715 |
| 0.00552 | 0.85456 | 0.00028618 |
| 0.00646 | 0.081755 | 0.00028282 |
| 0.00855 | 0.08567 | 0.00030075 |
| 0.01107 | 0.83865 | 0.00033241 |
| 0.01211 | 0.011888 | 0.0002402 |
| 0.01444 | 0.9996 | 0.00031735 |
| 0.0156 | 0.0064549 | 0.00020842 |
| 0.01774 | 1.76E-05 | 0.00030472 |
| 0.02002 | 0.39797 | 0.00026109 |
| 0.02219 | 0.045611 | 0.00026024 |
| 0.0245 | 2.61E-12 | 0.000033961 |
| 0.02717 | 0.42378 | 0.000025042 |
| 0.02867 | 0.60463 | 0.000028375 |
| 0.02961 | 0.069401 | 0.000028217 |
| 0.03169 | 0.085815 | 0.0003009 |
| 0.03422 | 0.83554 | 0.00033255 |
| 0.03526 | 0.011799 | 0.000024026 |
| 0.03759 | 0.9998 | 0.00031726 |
| 0.03875 | 0.0064592 | 0.000020825 |
| 0.04088 | 1.76E-05 | 0.00030483 |
| 0.04317 | 0.39805 | 0.00026105 |
| 0.04534 | 0.045621 | 0.00026018 |
| 0.04765 | 2.61E-12 | 0.00033967 |
| 0.05031 | 0.42371 | 0.00025049 |
| 0.05182 | 0.60489 | 0.00028366 |
| 0.05276 | 0.069407 | 0.00028214 |
| 0.05484 | 0.08585 | 0.00030079 |
| 0.05737 | 0.83566 | 0.00033249 |
| 0.05841 | 0.011794 | 0.00024032 |
| 0.06074 | 0.99998 | 0.00031721 |
| 0.0619 | 0.0064619 | 0.00020823 |
| 0.06403 | 1.76E-05 | 0.0003047 |
| 0.06632 | 0.39808 | 0.00026107 |
| 0.06849 | 0.045622 | 0.00026014 |
| 0.0708 | 2.61E-12 | 0.00033974 |
| 0.07346 | 0.42395 | 0.00025041 |
| 0.07497 | 0.60502 | 0.00028359 |
| 0.07591 | 0.069394 | 0.00028216 |
| 0.07799 | 0.085864 | 0.00030072 |
| 0.08052 | 0.83562 | 0.00033248 |
| 0.08155 | 0.011786 | 0.0002404 |
| 0.08389 | 0.99997 | 0.00031724 |
| 0.08505 | 0.0064617 | 0.00020827 |
| 0.08718 | 1.76E-05 | 0.00030467 |
| 0.08947 | 0.39799 | 0.00026111 |
| 0.09164 | 0.04561 | 0.00026017 |
| 0.09394 | 2.61E-12 | 0.00033977 |
| 0.09661 | 0.42406 | 0.00025036 |
| 0.09812 | 0.60499 | 0.0002836 |
| 0.09906 | 0.069364 | 0.00028223 |
| 0.10114 | 0.085856 | 0.00030068 |
| 0.10367 | 0.83543 | 0.00033255 |
| 0.1047 | 0.011795 | 0.00024025 |
| 0.10704 | 0.99975 | 0.00031731 |
| 0.1082 | 0.0064584 | 0.000208 |
| 0.11033 | 1.76E-05 | 0.000305 |
| 0.11262 | 0.3978 | 0.000261 |
| 0.11479 | 0.045585 | 0.00026 |
| 0.11709 | 2.61E-12 | 0.00034 |
| 0.11976 | 0.42403 | 0.00025 |
| 0.12127 | 0.6048 | 0.000284 |
| 0.1222 | 0.069362 | 0.000282 |
| 0.12429 | 0.085828 | 0.000301 |
| 0.12681 | 0.83512 | 0.000333 |
| 0.12785 | 0.0118 | 0.00024 |
| 0.13019 | 0.99934 | 0.000317 |
| 0.13135 | 0.0064522 | 0.000208 |
| 0.13348 | 1.76E-05 | 0.000305 |
| 0.13576 | 0.39783 | 0.000261 |
| 0.13793 | 0.045599 | 0.00026 |
| 0.14024 | 2.61E-12 | 0.00034 |
| 0.14291 | 0.42387 | 0.00025 |
| 0.14441 | 0.60447 | 0.000284 |
| 0.14535 | 0.069393 | 0.000282 |
| 0.14743 | 0.085796 | 0.000301 |
| 0.14996 | 0.83545 | 0.000333 |
| 0.151 | 0.0118 | 0.00024 |
| 0.15333 | 0.99967 | 0.000317 |
| 0.15449 | 0.0064573 | 0.000208 |
| 0.15663 | 1.76E-05 | 0.000305 |
| 0.15891 | 0.39801 | 0.000261 |
| 0.16108 | 0.045618 | 0.00026 |

FIG. 20

Class A waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.16339 | 2.61E-12 | 0.00033964 | 0.21688 | 0.085862 | 0.00030069 | 0.27023 | 0.0064549 | 0.000208 |
| 0.16606 | 0.42358 | 0.00025054 | 0.21941 | 0.83552 | 0.00033252 | 0.27237 | 1.76E-05 | 0.000305 |
| 0.16756 | 0.6048 | 0.00028369 | 0.22044 | 0.011792 | 0.00024027 | 0.27465 | 0.39795 | 0.000261 |
| 0.1685 | 0.069406 | 0.00028215 | 0.22278 | 0.99986 | 0.00031728 | 0.27682 | 0.045611 | 0.00026 |
| 0.17058 | 0.085839 | 0.00030083 | 0.22394 | 0.0064601 | 0.00020832 | 0.27913 | 2.61E-12 | 0.00034 |
| 0.17311 | 0.83563 | 0.00033251 | 0.22607 | 1.76E-05 | 0.00030465 | 0.2818 | 0.42371 | 0.00025 |
| 0.17415 | 0.011796 | 0.0002403 | 0.22836 | 0.39789 | 0.00026115 | 0.2833 | 0.60469 | 0.000284 |
| 0.17648 | 0.99993 | 0.00031722 | 0.23053 | 0.045596 | 0.00026025 | 0.28424 | 0.069403 | 0.000282 |
| 0.17764 | 0.0064612 | 0.00020822 | 0.23283 | 2.61E-12 | 0.0003397 | 0.28632 | 0.085824 | 0.000301 |
| 0.17977 | 1.76E-05 | 0.00030475 | 0.2355 | 0.42406 | 0.00025035 | 0.28885 | 0.83558 | 0.000333 |
| 0.18206 | 0.39808 | 0.00026106 | 0.23701 | 0.60489 | 0.00028363 | 0.28989 | 0.011799 | 0.00024 |
| 0.18423 | 0.045624 | 0.00026015 | 0.23794 | 0.069344 | 0.0002823 | 0.29222 | 0.99985 | 0.000317 |
| 0.18654 | 2.61E-12 | 0.00033971 | 0.24003 | 0.085842 | 0.00030075 | 0.29338 | 0.00646 | 0.000208 |
| 0.1892 | 0.42387 | 0.00025044 | 0.24256 | 0.83524 | 0.00033262 | 0.29551 | 1.76E-05 | 0.000305 |
| 0.19071 | 0.60499 | 0.00028361 | 0.24359 | 0.011799 | 0.00024022 | 0.2978 | 0.39807 | 0.000261 |
| 0.19165 | 0.069402 | 0.00028215 | 0.24593 | 0.99953 | 0.00031736 | 0.29997 | 0.045623 | 0.00026 |
| 0.19373 | 0.085861 | 0.00030074 | 0.24709 | 0.0064551 | 0.00020842 | 0.30228 | 2.61E-12 | 0.00034 |
| 0.19626 | 0.83565 | 0.00033248 | 0.24922 | 1.76E-05 | 0.00030466 | 0.30494 | 0.42377 | 0.00025 |
| 0.1973 | 0.011788 | 0.00024039 | 0.2515 | 0.39773 | 0.0002612 | 0.30645 | 0.60493 | 0.000284 |
| 0.19963 | 1 | 0.00031722 | 0.25367 | 0.045587 | 0.00026032 | 0.30739 | 0.069406 | 0.000282 |
| 0.20079 | 0.0064621 | 0.00020825 | 0.25598 | 2.61E-12 | 0.00033961 | 0.30947 | 0.085855 | 0.000301 |
| 0.20292 | 1.76E-05 | 0.00030467 | 0.25865 | 0.42395 | 0.00025036 | 0.312 | 0.83566 | 0.000332 |
| 0.20521 | 0.39804 | 0.00026109 | 0.26016 | 0.60462 | 0.00028373 | 0.31304 | 0.011792 | 0.00024 |
| 0.20738 | 0.045617 | 0.00026013 | 0.26109 | 0.069383 | 0.0002822 | 0.31537 | 0.99999 | 0.000317 |
| 0.20969 | 2.61E-12 | 0.00033979 | 0.26318 | 0.0858 | 0.00030092 | 0.31653 | 0.0064621 | 0.000208 |
| 0.21235 | 0.42403 | 0.00025038 | 0.2657 | 0.83534 | 0.00033261 | 0.31866 | 1.76E-05 | 0.000305 |
| 0.21386 | 0.60502 | 0.00028358 | 0.26674 | 0.011801 | 0.00024022 | 0.32095 | 0.39807 | 0.000261 |
| 0.2148 | 0.069378 | 0.00028218 | 0.26907 | 0.99951 | 0.00031734 | 0.32312 | 0.045621 | 0.00026 |

FIG. 21

Class A waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.32543 | 2.61E-12 | 0.00033976 | 0.37892 | 0.085819 | 0.00030085 | 0.43227 | 0.0064616 | 0.000208 |
| 0.32809 | 0.42398 | 0.00002504 | 0.38144 | 0.8352 | 0.00033264 | 0.4344 | 1.76E-05 | 0.000305 |
| 0.3296 | 0.60502 | 0.000283358 | 0.38248 | 0.0118 | 0.00024022 | 0.43669 | 0.39808 | 0.000261 |
| 0.33054 | 0.06939 | 0.00028216 | 0.38481 | 0.99932 | 0.0003174 | 0.43886 | 0.045623 | 0.00026 |
| 0.33262 | 0.085864 | 0.00030071 | 0.38597 | 0.006452 | 0.00020847 | 0.44117 | 2.61E-12 | 0.00034 |
| 0.33515 | 0.83559 | 0.00033249 | 0.38811 | 1.76E-05 | 0.0003047 | 0.44383 | 0.42391 | 0.00025 |
| 0.33618 | 0.011789 | 0.00024034 | 0.39039 | 0.39788 | 0.00026111 | 0.44534 | 0.605 | 0.000284 |
| 0.33852 | 0.99994 | 0.00031725 | 0.39256 | 0.045603 | 0.00026026 | 0.44628 | 0.069398 | 0.000282 |
| 0.33968 | 0.0064613 | 0.00020829 | 0.39487 | 2.61E-12 | 0.00033961 | 0.44836 | 0.085863 | 0.000301 |
| 0.34181 | 1.76E-05 | 0.00030467 | 0.39754 | 0.42382 | 0.00025039 | 0.45089 | 0.83564 | 0.000332 |
| 0.3441 | 0.39796 | 0.00026112 | 0.39904 | 0.60455 | 0.00028377 | 0.45193 | 0.011786 | 0.00024 |
| 0.34627 | 0.045606 | 0.00026019 | 0.39998 | 0.069397 | 0.00028218 | 0.45426 | 0.99999 | 0.000317 |
| 0.34857 | 2.61E-12 | 0.00033975 | 0.40206 | 0.085806 | 0.00030092 | 0.45542 | 0.006462 | 0.000208 |
| 0.35124 | 0.42406 | 0.00025036 | 0.40459 | 0.8355 | 0.00033256 | 0.45755 | 1.76E-05 | 0.000305 |
| 0.35275 | 0.60496 | 0.00028361 | 0.40563 | 0.0118 | 0.00024024 | 0.45984 | 0.39802 | 0.000261 |
| 0.35369 | 0.069355 | 0.00028226 | 0.40796 | 0.99974 | 0.00031727 | 0.46201 | 0.045614 | 0.00026 |
| 0.35577 | 0.085852 | 0.0003007 | 0.40912 | 0.0064583 | 0.00020828 | 0.46431 | 2.61E-12 | 0.00034 |
| 0.3583 | 0.83537 | 0.00033256 | 0.41126 | 1.76E-05 | 0.00030481 | 0.46698 | 0.42405 | 0.00025 |
| 0.35933 | 0.011797 | 0.00024023 | 0.41354 | 0.39804 | 0.00026105 | 0.46849 | 0.605 | 0.000284 |
| 0.36167 | 0.99969 | 0.00031732 | 0.41571 | 0.04562 | 0.00026018 | 0.46943 | 0.069371 | 0.000282 |
| 0.36283 | 0.0064574 | 0.00020838 | 0.41802 | 2.61E-12 | 0.00033965 | 0.47151 | 0.08586 | 0.000301 |
| 0.36496 | 1.76E-05 | 0.00030465 | 0.42068 | 0.42364 | 0.00025052 | 0.47404 | 0.83548 | 0.000333 |
| 0.36725 | 0.39774 | 0.00026121 | 0.42219 | 0.60485 | 0.00028367 | 0.47507 | 0.011794 | 0.00024 |
| 0.36942 | 0.045578 | 0.00026035 | 0.42313 | 0.069407 | 0.00028215 | 0.47741 | 0.99981 | 0.000317 |
| 0.37172 | 2.61E-12 | 0.00033964 | 0.42521 | 0.085845 | 0.00030081 | 0.47857 | 0.0064593 | 0.000208 |
| 0.37439 | 0.42401 | 0.00025035 | 0.42774 | 0.83565 | 0.0003325 | 0.4807 | 1.76E-05 | 0.000305 |
| 0.3759 | 0.60475 | 0.00028367 | 0.42878 | 0.011795 | 0.00024031 | 0.48299 | 0.39785 | 0.000261 |
| 0.37683 | 0.069369 | 0.00028224 | 0.43111 | 0.99996 | 0.00031721 | 0.48516 | 0.045591 | 0.00026 |

FIG. 22

Class A waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.48746 | 2.61E-12 | 0.00033968 | 0.54095 | 0.085832 | 0.00030085 | 0.59431 | 0.0064607 | 0.000208 |
| 0.49013 | 0.42405 | 0.00025035 | 0.54348 | 0.83561 | 0.00033252 | 0.59644 | 1.76E-05 | 0.000305 |
| 0.49164 | 0.60485 | 0.00028365 | 0.54452 | 0.011798 | 0.00024027 | 0.59873 | 0.39793 | 0.000261 |
| 0.49257 | 0.069353 | 0.00028227 | 0.54685 | 0.9999 | 0.00031723 | 0.6009 | 0.045601 | 0.00026 |
| 0.49466 | 0.085835 | 0.00030078 | 0.54801 | 0.0064606 | 0.00020822 | 0.6032 | 2.61E-12 | 0.00034 |
| 0.49719 | 0.83516 | 0.00033265 | 0.55014 | 1.76E-05 | 0.00030478 | 0.60587 | 0.42406 | 0.00025 |
| 0.49822 | 0.011799 | 0.00024023 | 0.55243 | 0.39808 | 0.00026105 | 0.60738 | 0.60493 | 0.000284 |
| 0.50056 | 0.99944 | 0.00031738 | 0.5546 | 0.045623 | 0.00026016 | 0.60832 | 0.069346 | 0.000282 |
| 0.50172 | 0.0064537 | 0.00020845 | 0.55691 | 2.61E-12 | 0.00033969 | 0.6104 | 0.085847 | 0.000301 |
| 0.50385 | 1.76E-05 | 0.00030467 | 0.55957 | 0.42382 | 0.00025046 | 0.61293 | 0.83531 | 0.000333 |
| 0.50613 | 0.39778 | 0.00026117 | 0.56108 | 0.60496 | 0.00028362 | 0.61396 | 0.011798 | 0.00024 |
| 0.5083 | 0.045593 | 0.00026029 | 0.56202 | 0.069404 | 0.00028215 | 0.6163 | 0.99961 | 0.000317 |
| 0.51061 | 2.61E-12 | 0.00033959 | 0.5641 | 0.085858 | 0.00030076 | 0.61746 | 0.0064563 | 0.000208 |
| 0.51328 | 0.42391 | 0.00025036 | 0.56663 | 0.83566 | 0.00033248 | 0.61959 | 1.76E-05 | 0.000305 |
| 0.51479 | 0.60455 | 0.00028376 | 0.56767 | 0.01179 | 0.00024037 | 0.62188 | 0.39769 | 0.000261 |
| 0.51572 | 0.069388 | 0.0002822 | 0.57 | 1 | 0.00031722 | 0.62404 | 0.045581 | 0.00026 |
| 0.51781 | 0.085789 | 0.00030096 | 0.57116 | 0.0064622 | 0.00020824 | 0.62635 | 2.61E-12 | 0.00034 |
| 0.52033 | 0.8354 | 0.00033259 | 0.57329 | 1.76E-05 | 0.00030468 | 0.62902 | 0.42398 | 0.00025 |
| 0.52137 | 0.011801 | 0.00024022 | 0.57558 | 0.39806 | 0.00026108 | 0.63053 | 0.60469 | 0.000284 |
| 0.5237 | 0.99959 | 0.00031731 | 0.57775 | 0.045619 | 0.00026013 | 0.63146 | 0.069376 | 0.000282 |
| 0.52486 | 0.0064561 | 0.00020834 | 0.58006 | 2.61E-12 | 0.00033977 | 0.63355 | 0.08581 | 0.000301 |
| 0.527 | 1.76E-05 | 0.00030476 | 0.58272 | 0.42401 | 0.00025039 | 0.63607 | 0.83527 | 0.000333 |
| 0.52928 | 0.39798 | 0.00026106 | 0.58423 | 0.60502 | 0.00028358 | 0.63711 | 0.011801 | 0.00024 |
| 0.53145 | 0.045615 | 0.00026021 | 0.58517 | 0.069384 | 0.00028217 | 0.63944 | 0.99942 | 0.000317 |
| 0.53376 | 2.61E-12 | 0.00033964 | 0.58725 | 0.085863 | 0.0003007 | 0.6406 | 0.0064535 | 0.000208 |
| 0.53643 | 0.42365 | 0.0002505 | 0.58978 | 0.83556 | 0.0003325 | 0.64274 | 1.76E-05 | 0.000305 |
| 0.53793 | 0.60475 | 0.00028837 | 0.59081 | 0.01179 | 0.00024031 | 0.64502 | 0.39792 | 0.000261 |
| 0.53887 | 0.069405 | 0.00028215 | 0.59315 | 0.99991 | 0.00031726 | 0.64719 | 0.045608 | 0.00026 |

FIG. 23

Class A waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.6495 | 2.61E-12 | 0.00033962 | 0.70299 | 0.085864 | 0.00030072 | 0.75635 | 0.0064522 | 0.000208 |
| 0.65217 | 0.42377 | 0.00025042 | 0.70552 | 0.83562 | 0.00033248 | 0.75848 | 1.76E-05 | 0.000305 |
| 0.65367 | 0.60462 | 0.00028375 | 0.70655 | 0.011786 | 0.0002404 | 0.76076 | 0.39783 | 0.000261 |
| 0.65461 | 0.069401 | 0.00028217 | 0.70889 | 0.99997 | 0.00031724 | 0.76293 | 0.045599 | 0.00026 |
| 0.65569 | 0.085815 | 0.0003009 | 0.71005 | 0.0064617 | 0.00020827 | 0.76524 | 2.61E-12 | 0.00034 |
| 0.65922 | 0.83554 | 0.00033255 | 0.71218 | 1.76E-05 | 0.00030467 | 0.76791 | 0.42387 | 0.00025 |
| 0.66026 | 0.011799 | 0.00024026 | 0.71447 | 0.39799 | 0.00026111 | 0.76941 | 0.60447 | 0.000284 |
| 0.66259 | 0.9998 | 0.00031726 | 0.71664 | 0.04561 | 0.00026017 | 0.77035 | 0.069393 | 0.000282 |
| 0.66375 | 0.0064592 | 0.00020825 | 0.71894 | 2.61E-12 | 0.00033977 | 0.77243 | 0.085796 | 0.000301 |
| 0.66588 | 1.76E-05 | 0.00030483 | 0.72161 | 0.42406 | 0.00025036 | 0.77496 | 0.83545 | 0.000333 |
| 0.66817 | 0.39805 | 0.00026105 | 0.72312 | 0.60499 | 0.0002836 | 0.776 | 0.0118 | 0.00024 |
| 0.67034 | 0.045521 | 0.00026018 | 0.72406 | 0.069364 | 0.00028223 | 0.77833 | 0.99967 | 0.000317 |
| 0.67265 | 2.61E-12 | 0.00033967 | 0.72614 | 0.085856 | 0.00030068 | 0.77949 | 0.0064573 | 0.000208 |
| 0.67531 | 0.42371 | 0.00025049 | 0.72867 | 0.83543 | 0.00033255 | 0.78163 | 1.76E-05 | 0.000305 |
| 0.67682 | 0.60489 | 0.00028366 | 0.7297 | 0.011795 | 0.00024025 | 0.78391 | 0.39801 | 0.000261 |
| 0.67776 | 0.069407 | 0.00028214 | 0.73204 | 0.99975 | 0.00031731 | 0.78608 | 0.045618 | 0.00026 |
| 0.67984 | 0.08585 | 0.00030079 | 0.7332 | 0.0064584 | 0.00020836 | 0.78839 | 2.61E-12 | 0.00034 |
| 0.68237 | 0.83566 | 0.00033249 | 0.73533 | 1.76E-05 | 0.00030465 | 0.79106 | 0.42358 | 0.000251 |
| 0.68341 | 0.011794 | 0.00024032 | 0.73762 | 0.3978 | 0.00026119 | 0.79256 | 0.6048 | 0.000284 |
| 0.68574 | 0.99998 | 0.00031721 | 0.73979 | 0.045585 | 0.00026031 | 0.7935 | 0.069406 | 0.000282 |
| 0.6869 | 0.0064619 | 0.00020823 | 0.74209 | 2.61E-12 | 0.00033967 | 0.79558 | 0.085839 | 0.000301 |
| 0.68903 | 1.76E-05 | 0.0003047 | 0.74476 | 0.42403 | 0.00025035 | 0.79811 | 0.83563 | 0.000333 |
| 0.69132 | 0.39808 | 0.00026107 | 0.74627 | 0.6048 | 0.00028366 | 0.79915 | 0.011796 | 0.00024 |
| 0.69349 | 0.045622 | 0.00026014 | 0.7472 | 0.069362 | 0.00028225 | 0.80148 | 0.99993 | 0.000317 |
| 0.6958 | 2.61E-12 | 0.00033974 | 0.74929 | 0.085828 | 0.00030081 | 0.80264 | 0.0064612 | 0.000208 |
| 0.69846 | 0.42395 | 0.00025041 | 0.75181 | 0.83512 | 0.00033267 | 0.80477 | 1.76E-05 | 0.000305 |
| 0.69997 | 0.60502 | 0.00028359 | 0.75285 | 0.0118 | 0.00024022 | 0.80706 | 0.39808 | 0.000261 |
| 0.70091 | 0.069394 | 0.00028216 | 0.75519 | 0.99934 | 0.0003174 | 0.80923 | 0.045624 | 0.00026 |

FIG. 24

Class A waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.81154 | 2.61E-12 | 0.00033971 | 0.86503 | 0.085842 | 0.00030075 | 0.91838 | 0.00646 | 0.000208 |
| 0.8142 | 0.42387 | 0.00025044 | 0.86756 | 0.83524 | 0.00033262 | 0.92051 | 1.76E-05 | 0.000305 |
| 0.81571 | 0.60499 | 0.00028361 | 0.86859 | 0.011799 | 0.00024022 | 0.9228 | 0.39807 | 0.000261 |
| 0.81665 | 0.069402 | 0.00028215 | 0.87093 | 0.99953 | 0.00031736 | 0.92497 | 0.045623 | 0.00026 |
| 0.81873 | 0.085861 | 0.00030074 | 0.87209 | 0.0064551 | 0.00020842 | 0.92728 | 2.61E-12 | 0.00034 |
| 0.82126 | 0.83565 | 0.00033248 | 0.87422 | 1.76E-05 | 0.00030466 | 0.92994 | 0.42377 | 0.00025 |
| 0.8223 | 0.011788 | 0.00024039 | 0.8765 | 0.39773 | 0.0002612 | 0.93145 | 0.60493 | 0.000284 |
| 0.82463 | 1 | 0.00031722 | 0.87867 | 0.045587 | 0.00026032 | 0.93239 | 0.069406 | 0.000282 |
| 0.82579 | 0.0064621 | 0.00020825 | 0.88098 | 2.61E-12 | 0.00033961 | 0.93447 | 0.085855 | 0.000301 |
| 0.82792 | 1.76E-05 | 0.00030467 | 0.88365 | 0.42395 | 0.00025036 | 0.937 | 0.83566 | 0.000332 |
| 0.83021 | 0.39804 | 0.00026109 | 0.88516 | 0.60462 | 0.00028373 | 0.93804 | 0.011792 | 0.00024 |
| 0.83238 | 0.045617 | 0.00026013 | 0.88609 | 0.069383 | 0.0002822 | 0.94037 | 0.99999 | 0.000317 |
| 0.83469 | 2.61E-12 | 0.00033979 | 0.88818 | 0.0858 | 0.00030092 | 0.94153 | 0.0064621 | 0.000208 |
| 0.83735 | 0.42403 | 0.00025038 | 0.8907 | 0.83534 | 0.00033261 | 0.94366 | 1.76E-05 | 0.000305 |
| 0.83886 | 0.60502 | 0.00028358 | 0.89174 | 0.011801 | 0.00024022 | 0.94595 | 0.39807 | 0.000261 |
| 0.8398 | 0.069378 | 0.00028218 | 0.89407 | 0.99951 | 0.00031734 | 0.94812 | 0.045621 | 0.00026 |
| 0.84188 | 0.085862 | 0.00030069 | 0.89523 | 0.0064549 | 0.00020838 | 0.95043 | 2.61E-12 | 0.00034 |
| 0.84441 | 0.83552 | 0.00033252 | 0.89737 | 1.76E-05 | 0.00030474 | 0.95309 | 0.42398 | 0.00025 |
| 0.84544 | 0.011792 | 0.00024027 | 0.89965 | 0.39795 | 0.00026108 | 0.9546 | 0.60502 | 0.000284 |
| 0.84778 | 0.99986 | 0.00031728 | 0.90182 | 0.045611 | 0.00026023 | 0.95554 | 0.069939 | 0.000282 |
| 0.84894 | 0.0064601 | 0.00020832 | 0.90413 | 2.61E-12 | 0.00033963 | 0.95762 | 0.085864 | 0.000301 |
| 0.85107 | 1.76E-05 | 0.00030465 | 0.9068 | 0.42371 | 0.00025046 | 0.96015 | 0.83559 | 0.000332 |
| 0.85336 | 0.39789 | 0.00026115 | 0.9083 | 0.60469 | 0.00028372 | 0.96118 | 0.011789 | 0.00024 |
| 0.85553 | 0.045596 | 0.00026025 | 0.90924 | 0.069403 | 0.00028216 | 0.96352 | 0.99994 | 0.000317 |
| 0.85783 | 2.61E-12 | 0.0003397 | 0.91132 | 0.085824 | 0.00030087 | 0.96468 | 0.0064613 | 0.000208 |
| 0.8605 | 0.42406 | 0.00025035 | 0.91385 | 0.83558 | 0.00033253 | 0.96681 | 1.76E-05 | 0.000305 |
| 0.86201 | 0.60489 | 0.00028363 | 0.91489 | 0.011799 | 0.00024026 | 0.9691 | 0.39796 | 0.000261 |
| 0.86294 | 0.069344 | 0.0002823 | 0.91722 | 0.99985 | 0.00031725 | 0.97127 | 0.045606 | 0.00026 |

FIG. 25

Class A waveform

| time (sec) | local peak amplitude (normalized to waveform peak) | half-height interval (sec) | time (sec) | local peak amplitude (normalized to waveform peak) | half-height interval (sec) | time (sec) | local peak amplitude (normalized to waveform peak) | half-height interval (sec) |
|---|---|---|---|---|---|---|---|---|
| 0.97357 | 2.61E-12 | 0.00033975 | | | | | | |
| 0.97624 | 0.42406 | 0.00025036 | | | | | | |
| 0.97775 | 0.60496 | 0.00028361 | | | | | | |
| 0.97869 | 0.069355 | 0.00028226 | | | | | | |
| 0.98077 | 0.085852 | 0.0003007 | | | | | | |
| 0.9833 | 0.83537 | 0.00033256 | | | | | | |
| 0.98433 | 0.011797 | 0.00024023 | | | | | | |
| 0.98667 | 0.99969 | 0.00031732 | | | | | | |
| 0.98783 | 0.0064574 | 0.00020838 | | | | | | |
| 0.98996 | 1.76E-05 | 0.00030465 | | | | | | |
| 0.99225 | 0.39774 | 0.00026121 | | | | | | |
| 0.99442 | 0.045578 | 0.00026035 | | | | | | |
| 0.99672 | 2.61E-12 | 0.00033964 | | | | | | |
| 0.99939 | 0.42401 | 0.00025035 | | | | | | |

METHODS AND SYSTEMS OF USING [[PEMF]] ELECTROMAGNETIC FIELD STIMULATION TO INCREASE HEAT SHOCK PROTEIN EXPRESSION IN A MAMMAL

CLAIM OF BENEFIT TO PRIOR APPLICATIONS

This application hereby claims the benefit of and priority to U.S. Non-Provisional application Ser. No. 17/327,279, entitled "METHODS AND DEVICES FOR USING PULSED RADIOFREQUENCY ELECTROMAGNETIC FIELD STIMULATION TO REDUCE INFLAMMATION" which was filed May 21, 2021, all of which is incorporated herein by reference in its entirety.

FIELD OF THE DISCLOSURE

The inventions of the present disclosure relate generally to providing methods and devices using pulsed or pulsing electromagnetic fields (PEMF) to provide various health related benefits and advantages. More specifically, the inventions of the present disclosure include providing improved PEMF signals, methods, devices and systems that reduce inflammation, increase heat shock protein expression and provide a variety of other health related benefits and advantages.

GENERAL BACKGROUND

Inflammation is the biological response of body tissues to harmful stimuli, such as pathogens, damaged cells, or irritants (Ferrero-Miliani 2007). The five cardinal diagnostic signs of inflammation in humans and animals (redness, heat, swelling, pain and loss of function) are understood to be caused by increased blood flow, vasodilation, cellular metabolism, soluble mediator release, extravasation of fluids and cellular influx (Ferrero-Miliani 2007). Acute inflammation occurring immediately upon injury plays protective roles in the immediate response to injury, and is generally resolved upon recovery (Freire 2000). However, inadequate resolution of inflammation and failure to bring tissue to homeostasis results in destruction of cells and tissues, resulting in chronic inflammation (Freire 2000). Often undiagnosed, chronic inflammation is the cause of the majority of human disease (Dinarello 2012), including atherosclerosis, cancer, autoimmunity and chronic infections, and is a major contributor in age-related conditions including Alzheimer's disease (Griffin 2013, Netea 2017), playing causative roles in type 2 diabetes, nonalcoholic fatty liver disease, hypertension, cardiovascular disease (CVD), chronic kidney disease, various types of cancer, metabolic syndrome (hypertension, hyperglycemia and dyslipidemia), depression, neurodegenerative and autoimmune diseases, osteoporosis, and sarcopenia (Furman 2019).

Many pharmacological treatments targeting the molecular mechanisms governing inflammation are in worldwide clinical use today, including anti-cytokine treatments which reduce inflammation by reducing the expression of inflammatory cytokines by cells (Kany 2019, Turner 2014, Garth 2018, Furman 2019).

Inflammatory cytokines are small secreted proteins (<40 kDa) released by nearly every type of cell in response to harmful stimuli triggering inflammation (Kany 2019, Turner 2014, Garth 2018, Furman 2019) which are key regulators responsible for pathological pain in acute inflammation and chronic inflammation responsible for inflammatory diseases (Zhang 2007, Turner 2014). Pro-inflammatory cytokines increase inflammation: increases in pro-inflammatory cytokines increase the expression of corresponding genes directing cells to increase inflammation via autocrine, paracrine, and endocrine functions (Turner 2014, Garth 2018), causing both the clinical diagnostic symptoms of acute inflammation and often-undiagnosed chronic inflammation (Ferrero-Miliani 2007, Garth, 2018).

Anti-cytokine therapies reduce the expression of pro-inflammatory cytokines thus reducing inflammation, and key pro-inflammatory cytokine targeted therapeutically are IL-1 (IL1-1α, IL-1β), Il-6, and TNF (TNF-α, TNF-β) (Zhang 2007, Cavalli 2012, Gao 2010, Kany 2019). Anti-IL-1 therapies, which neutralize IL-pro-inflammatory cytokines in animals and humans have been shown to reduce inflammation in animals and humans (Dinarello 2012). IL-1 regulates the pathogenesis of numerous conditions characterized by organ or tissue inflammation have been suggested for treating a broad spectrum of inflammatory diseases (Dinarello 2012), and anti IL-1a therapies have been suggested for conditions affecting the lung and respiratory tract, dermatoses and inflammatory skin disorders, systemic sclerosis, myocarditis, pericarditis, myocardial infarction, coronary artery disease, inflammatory thrombosis, COVID-19, vasculitis, Kawasaki disease, Behcet's syndrome, Sjogren Syndrome, and cancer (Cavalli 2021). Anti-TNF-a therapies intended to reduce levels of TNF in animals and humans are clinical use for diseases such as rheumatoid arthritis, Crohn's disease, ulcerative colitis, psoriasis, psoriatic arthritis, ankylosing spondylitis (Monaco 2014). Recently, anti-TNF therapies have been urgently recommended to neutralize COVID-19 cytokine release syndrome (Robinson 2021).

Heat shock proteins are a class of proteins which serve key functions in the cellular response to stressors, and during wound healing and tissue remodeling (Laplante 1998). Heat shock proteins (HSP60, HSP70, and HSP90) modulate inflammation and oxidative stress (Jacquier-Sarlin 1994) and have been shown to prevent or arrest inflammatory damage (Hauet-Broere 2006) and triggers tissue regeneration and wound healing by regulating inflammation and cell proliferation (Pei 2016). Moreover, PEMF can enhance Hsp70 expression following spinal cord injury[24]. Therefore, we also checked the expression levels of genes encoding heat shock proteins, Hsp90aa (Heat Shock Protein 90 Alpha Family Class A Member 1, encoding inducible HSP90), Hspd1 (Heat Shock Protein Family D (Hsp60) Member 1, encoding HSP70), and Hspa1a (Heat Shock Protein Family A (Hsp70) Member 1A, encoding HSP70).

Nonthermal pulsed electromagnetic fields, from low frequency to pulse-modulated radio frequency, have a long history as FDA-cleared specific adjunctive therapies, beginning with the treatment of delayed and non-union fractures, fresh fractures and chronic wounds more than 40 years ago. A broad range of time-varying electromagnetic fields, referred to as pulsing radiofrequency fields (PRF), particularly in the 15-40 MHz range, have been shown to enhance wound healing when used as adjunctive therapy for a variety of surgical procedures and musculoskeletal injuries (Pilla 2006, Rohde 2010, Rohde 2015).

Nonthermal PRF electromagnetic fields, produce therapeutic benefits by inducing biologically active electric fields for which heating of target tissue is negligible (Pilla 2006), and have been used successfully as adjunctive therapy to accelerate the repair of delayed and nonunion fractures and chronic wounds, and for the reduction of pain and inflammation (Basset 1977, Aaron 2004, Pilla 2006, Guo 2012, Ross 2013). Recent double-blind, placebo controlled randomized clinical trials have reported that disposable PRF devices, applied immediately postoperatively, significantly accelerated pain reduction and reduced postoperative narcotic requirements after breast augmentation (Hedén 2008, Rawe 2012) and reduction (Rohde 2010), including significantly reduced interleukin-1β in wound exudates, and reduced wound exudate volume, which are reliable markers of inflammation (Rohde 2010, 2015). Since these clinical reports, basic studies have continued to demonstrate that pulsed electromagnetic fields can up-regulate calmodulin-dependent nitric oxide/cyclic guanosine monophosphate signaling (Pilla 2011, 2012.

Significant improvements in pain and edema (Dortsch 2006), angiogenesis (Roland 2000, Weber 2004, Tepper 2004, Delle Monache 2008) and tissue repair (Strauch 2006, Callaghan 2007, Strauch 2007) have been demonstrated in animal models using PRF. As an example, employing a Carrageenan-induced rat paw edema model, a standard pharmacological model, Johnson et al. showed statistically significant effectiveness of PRF (three 15-minute treatments, two hours apart) in reducing both pain and swelling (Johnson 2008).

The magnetic component of nonthermal PRF and PEMF signals penetrates all biological tissues without attenuation, offering a noninvasive means of delivering these EMF therapies to the body. PRF signals in clinical use today are capable of inducing electrical fields in bodily tissues, driving the therapeutic effects in a manner dependent upon signal spectral and timing characteristics (Pilla 2006). In the early 2000's, an increased understanding of the mechanisms of action underlying PRF therapies stimulated the development of low-cost portable PEMF devices: lower-power signals with 50 mGauss (mG) peak magnetic field amplitude developed by Arthur Pilla and David Muehsam performed equally well as the previous 2.0 Gauss technologies, leading to the 2008 FDA clearance for the Ivivi Sofpulse devices. Since that time, this new generation of low-power PRF therapies rapidly become a standard part of surgical care, and new, more significant, clinical applications for osteoarthritis (Wu, 2018; Wang 2019), brain and cardiac ischemia (Pena-Philippides, 2014; Hao, 2014) and traumatic brain injury (Rasouli 2012) and other conditions are in the pipeline. Previous studies using FDA-cleared PRF devices strongly support the use of this class of signals for enhancing growth and repair processes (Pilla 2011).

The full range of biological effects due to changes in waveform features remains to be fully explored, and these previous results demonstrate that a better understanding can guide the development of more effective signals and devices targeting particular conditions. Accordingly, in at least one embodiment of the present invention, the inventors developed signals and devices that are more effective at reducing pro-inflammatory cytokine expression in a cell model for inflammation.

In order to produce a better understanding of the effect of PRF waveform features on pro-inflammatory cytokine levels, a mouse BV-2 microglial cell model for inflammation and regeneration/repair/regrowth was chosen to evaluate the anti-inflammatory, regenerative properties and other benefits and advantages of several different PRF signal variants. After extensive testing of various signals and signal parameters for efficacy, eleven different signals were tested, and the effects of different PRF signals on microglial inflammatory profiles, were assessed using real-time PCR. To assess the effect of PRF signals on inflammation, cells were activated with bacterial endotoxin lipopolysaccharide (LPS) to induce an inflammatory response (Bachiller 2018) resulting in increased expression of anti- and pro-inflammatory chemokines (Ye 2020). Here, the effects of different PRF signals on mRNA levels for pro-inflammatory cytokines (IL-1a, IL-1β, TNF a, IL-6) were assessed using real-time PCR, Levels of expression were also checked for genes encoding heat shock proteins, Hsp90aa (Heat Shock Protein 90 Alpha Family Class A Member 1, encoding inducible HSP90), Hspd1 (Heat Shock Protein Family D (Hsp60) Member 1, encoding HSP70), and Hspa1a (Heat Shock Protein Family A (Hsp70) Member 1A, encoding HSP70).

The studies performed and the resulting data obtained from those studies shown and described herein demonstrate specific PRF signals and PRF signal variants that provided enhanced benefits compared to previous technologies, signals and signal variants. As an example and not by way of limitation, one or more of PRF signals and the associated method disclosed herein is able to reduce upregulation of mRNA expression of pro-inflammatory cytokines.

The results shown herein show, among other things, that several new PRF signals reduce inflammation in vitro cell culture model of LPS activated BV-2 microglial cells.

REFERENCES

Aaron R K, Ciombor D M, Simon B J. Treatment of nonunions with electric and electromagnetic fields. Clin Orthop Relat Res. 2004; 419:21-29.

Aaron R K, Ciombor D M, Wang S, Simon B. Clinical biophysics: the promotion of skeletal repair by physical forces. Ann N Y Acad Sci. 2006; 1068:513-531.

Bachiller S, Jiménez-Ferrer I, Paulus A, et al. Microglia in Neurological Diseases: A Road Map to Brain-Disease Dependent-Inflammatory Response. Front Cell Neurosci. 2018; 12:488.

Basset C A, Pilla A A, Pawluk R. A non-surgical salvage of surgically-resistant pseudoarthroses and non-unions by pulsing electromagnetic fields. Clin Orthop Relat Res. 1977; 124:117-131. Bioelectromagnetics 29:640-648.

Callaghan M J, Chang E I, Seiser N, Aarabi S, Ghali S, Kinnucan E R, Simon B J, Gurtner G C (2008). Pulsed electromagnetic fields accelerate normal and diabetic wound healing by increasing endogenous FGF-2 release. Plast Reconstr Surg 121:130-141.

Cavalli G, Colafrancesco S, Emmi G, et al. Interleukin 1α: a comprehensive review on the role of IL-1α in the pathogenesis and treatment of autoimmune and inflammatory diseases. Autoimmun Rev. 2021; 20(3):102763.

Dinarello C A, Simon A, van der Meer J W. Treating inflammation by blocking interleukin-1 in a broad spectrum of diseases. Nat Rev Drug Discov. 2012; 11(8):633-652.

Diniz P, Shomura K, Soejima K, Ito G. Effects of pulsed electromagnetic field (PEMF) stimulation on bone tissue like formation are dependent on the maturation stages of the osteoblasts. Bioelectromagnetics 2002; 23:398-405.

Dortch A B, Johnson M T. Characterization of pulsed magnetic field therapy in a rat model for rheumatoid arthritis. Biomed Sci Instrum. 2006; 42:302-307. Electromagnetic fields (ELF-EMFs) induce in vitro angiogenesis process in human endothelial cells. Electromagnetic fields increase in vitro and in vivo angiogenesis through endothelial release of FGF-2.

Faas G C, Raghavachari S, Lisman J E, Mody I. Calmodulin as a direct detector of Ca2+ signals. Nat Neurosci. 2011; 14:301-304. 13. Bredt D S, Snyder S H. Isolation of nitric oxide synthetase, a calmodulin-requiring enzyme. Proc Natl Acad Sci USA. 1990; 87:682-685. FASEB J 18:1231-1233.

Ferrero-Miliani L, Nielsen O H, Andersen P S, Girardin S E. Chronic inflammation: importance of NOD2 and NALP3 in interleukin-1beta generation. Clin Exp Immunol. 2007; 147(2):227-235.

Fini M, Torricelli P, Giavaresi G, et al. Effect of pulsed electromagnetic field stimulation on knee cartilage, sub-chondral and epyphiseal trabecular bone of aged Dunkin Hartley guinea pigs. Biomed Pharmacother. 2008; 62(10): 709-715.

Freire M O, Van Dyke T E. Natural resolution of inflammation. Periodontol 2000. 2013; 63(1):149-164.

Furman D, Campisi J, Verdin E, et al. Chronic inflammation in the etiology of disease across the life span. Nat Med. 2019; 25(12):1822-1832.

Gao X, Picchi A, Zhang C. Upregulation of TNF-alpha and Receptors Contribute to Endothelial Dysfunction in Zucker Diabetic Rats. Am J Biomed Sci. 2010; 2(1):1-12.

Garth J, Barnes J W, Krick S. Targeting Cytokines as Evolving Treatment Strategies in Chronic Inflammatory Airway Diseases. Int J Mol Sci. 2018; 19(11):3402.

Goto T, Fujioka M, Ishida M, Kuribayashi M, Ueshima K, Kubo T. Noninvasive upregulation of angiopoietin-2 and fibroblast growth factor-2 in bone marrow by pulsed electromagnetic field therapy. J Orthop Sci. 2010; 15:661-665.

Guo L, Kubat N J, Nelson T R, Isenberg R A. Meta-analysis of clinical efficacy of pulsed radio frequency energy treatment. Ann Surg. 2012; 255:457-467.

Griffin W S. Neuroinflammatory cytokine signaling and Alzheimer's disease. N Engl J Med. 2013; 368(8):770-771.

Hauet-Broere F, Wieten L, Guichelaar T, Berlo S, van der Zee R, Van Eden W. Heat shock proteins induce T cell regulation of chronic inflammation. Ann Rheum Dis. 2006; 65 Suppl 3(Suppl 3):iii65-iii68.

Hedén P, Pilla A A. Effects of pulsed electromagnetic fields on postoperative pain: A double-blind randomized pilot study in breast augmentation patients. Aesthetic Plast Surg. 2008; 32:660-666. Increases tensile strength in a rat Achilles' tendon repair model. J Hand Surg 31:1131-1135.

Jacquier-Sarlin M R, Fuller K, Dinh-Xuan A T, Richard M J, Polla B S. Protective effects of hsp70 in inflammation. Experientia. 1994; 50(11-12):1031-1038.

Johnson, et al. 2008. Modulation of carrageenan-induced paw edema and hyperalgesia in the rat with pulsed magnetic field therapy. Bioelectromagnetics Society Meeting, June 2008. San Diego, CA Kany S, Vollrath J T, Relja B. Cytokines in Inflammatory Disease. Int J Mol Sci. 2019; 20(23):6008.

Kim S S, Shin H J, Eom D W, et al. Enhanced expression of neuronal nitric oxide synthase and phospholipase C-gamma1 in regenerating murine neuronal cells by pulsed electromagnetic field. Exp Mol Med. 2002; 34(1): 53-59. doi:10.1038/emm.2002.8. Microsurgically transferred vessel. Plast Reconstr Surg 105:1371-1374.

Laplante A F, Moulin V, Auger F A, et al. Expression of heat shock proteins in mouse skin during wound healing. J Histochem Cytochem. 1998; 46(11):1291-1301.

Lively S, Schlichter L C. Microglia Responses to Pro-inflammatory Stimuli (LPS, IFNγ+TNFα) and Repro-gramming by Resolving Cytokines (IL-4, IL-10). Front Cell Neurosci. 2018; 12:215.

Michaud M, Balardy L, Moulis G, et al. Proinflammatory cytokines, aging, and age-related diseases. J Am Med Dir Assoc. 2013; 14(12):877-882.

Miura M, Okada J. Non-thermal vasodilatation by radio frequency burst-type electromagnetic field radiation in the frog. J Physiol. 1991; 435:257-273.

Moffett J, Fray L M, Kubat N J. Activation of endogenous opioid gene expression in human keratinocytes and fibroblasts by pulsed radiofrequency energy fields. J Pain Res. 2012; 12:347-357.

Monaco C, Nanchahal J, Taylor P, Feldmann M. Anti-TNF therapy: past, present and future. Int Immunol. 2015; 27(1):55-62.

Netea M G, Balkwill F, Chonchol M, et al. A guiding map for inflammation. Nat Immunol. 2017 Jul. 19; 18(8): 826-831.

Pei W, Tanaka K, Huang S C, et al. Extracellular HSP60 triggers tissue regeneration and wound healing by regulating inflammation and cell proliferation. NPJ Regen Med. 2016; 1:16013.

Pena-Philippides J C, Hagberg S, Nemoto E, Roitbak T. Effect of pulsed electromagnetic field (PEMF) on LPS-induced chronic inflammation in mice. In: Markov M, ed. Electromagnetic Fields in Biology and Medicine. Boca Raton, Fla.: CRC Press; 2015:164-172.

Pena-Philippides J C, Yang Y, Bragina O, Hagberg S, Nemoto E, Roitbak T. Effect of pulsed electromagnetic field (PEMF) on infarct size and inflammation after cerebral ischemia in mice. Transl Stroke Res. 2014; 5:491-500.

Pilla A A, Fitzsimmons R J, Muehsam D J, Rohde C, Wu J K, Casper D. Electromagnetic fields as first messenger in biological signaling: Application to calmodulin-dependent signaling in tissue repair. Biochim Biophys Acta 2011; 10:1236-1245.

Pilla A A. Electromagnetic fields instantaneously modulate nitric oxide signaling in challenged biological systems. Biochem Biophys Res Commun. 2012; 426:330-333.

Pilla A A. Mechanisms and therapeutic applications of time varying and static magnetic fields. In: Barnes F, Greenebaum B, eds. Biological and Medical Aspects of Electromagnetic Fields. Boca Raton, Fla.: CRC Press; 2006: 351-411.

Rasouli J, Lekhraj R, White N M, et al. Attenuation of inter-leukin-1beta by pulsed electromagnetic fields after traumatic brain injury. Neurosci Lett. 2012; 519:4-8.

Rawe I M, Lowenstein A, Barcelo C R, Genecov D G. Control of postoperative pain with a wearable continuously operating pulsed radiofrequency energy device: A preliminary study. Aesthetic Plast Surg. 2012; 36:458-463.

Ren K, Torres R. Role of interleukin-1beta during pa in and inflammation. Brain Res Rev. 2009; 60:57-64.

Robinson P C, Richards D, Tanner H L, Feldmann M. Accumulating evidence suggests anti-TNF therapy needs to be given trial priority in COVID-19 treatment. Lancet Rheumatol. 2020; 2(11):e653-e655.

Rohde C, Chiang A, Adipojou O, Casper D, Pilla A A. Effects of pulsed electromagnetic fields on IL-1β and post-operative pain: A double-blind, placebo-controlled pilot study in breast reduction patients. Plast Reconstr Surg. 2010; 125:1620-1629.

Rohde C, Taylor E, Pilla A. Pulsed electromagnetic fields accelerate reduction of post-operative pain and inflammation: Application to plastic and reconstructive surgical procedures. In: Markov M, ed. Electromagnetic Fields in Biology and Medicine. Boca Raton, Fla.: CRC Press; 2015:297-309.

Roland D, Ferder M S, Kothuru R, Faierman T, Strauch B (2000).

Ross C L, Harrison B S. The use of magnetic field for the reduction of inflammation: A review of the history and therapeutic results. Altern Ther Health Med. 2013; 19:47-54.

Schnoke M, Midura R J. Pulsed electromagnetic fields rapidly modulate intracellular signaling events in osteoblastic cells: comparison to parathyroid hormone and insulin. J Orthop Res. 2007; 25(7):933-940. doi:10.1002/jor.20373.

Strauch B, Patel M K, Navarro J A, Berdichevsky M, Yu H L, Pilla A A. Pulsed magnetic fields accelerate cutaneous wound healing in rats. Plast Reconstr Surg. 2007; 120(2): 425-430. doi:10.1097/01.prs.0000267700.15452.d0.

Strauch B, Patel M K, Rosen D J, Mahadevia S, Brindzei N, Pilla A A (2006). Pulsed magnetic field therapy.

Tepper O M, Callaghan M J, Chang E I, et al. Electromagnetic fields increase in vitro and in vivo angiogenesis through endothelial release of FGF-2. FASEB J. 2004; 18:1231-1233.

Weber R V, Navarro A, Wu J K, Yu H L, Strauch B (2005). Pulsed magnetic fields applied to a transferred arterial loop support the rat groin composite flap. Plast Reconstr Surg 114:1185-1189.

Turner M D, Nedjai B, Hurst T, Pennington D J. Cytokines and chemokines: At the crossroads of cell signalling and inflammatory disease. Biochim Biophys Acta. 2014; 1843 (11):2563-2582.

Werner S, Grose R. Regulation of wound healing by growth factors and cytokines. Physiol Rev. 2003; 83:835-870.

Ye X, Zhu M, Che X, et al. Lipopolysaccharide induces neuroinflammation in microglia by activating the MTOR pathway and downregulating Vps34 to inhibit autophagosome formation. J Neuroinflammation. 2020; 17(1):18.

Zhang J M, An J. Cytokines, inflammation, and pain. Int Anesthesiol Clin. 2007; 45(2):27-37.

SUMMARY

In one embodiment of the present disclosure, a method for reducing inflammation in a mammal is provided. The method includes providing to a mammal in need thereof one or more signals that reduces inflammation in the mammal using a device that generates the one or more signals. The device comprises a power supply, an amplifier, an antenna and a waveform generator where the one or more signals provided have an aperiodic continuous waveform function or an aperiodic pulse train.

In another embodiment of the present disclosure, a method of increasing heat shock protein expression in a mammal is provided. The method includes providing to a mammal in need thereof one or more signals having a continuous function or an aperiodic pulse train that increases heat shock protein expression in the mammal in need thereof.

In yet another embodiment of the present disclosure, the device also includes a battery or the power supply is a battery used to power the device.

In yet another embodiment of the present disclosure, a device for reducing inflammation in a mammal is provided. The device comprises a power supply, an amplifier, an antenna and a waveform generator where the device generates one or more signals having a continuous waveform function or an aperiodic pulse train that reduce inflammation in a mammal in need thereof.

In at least one aspect at of least one embodiment of the present disclosure, the one or more signals also have a variable local peak level or a non-constant repetition frequency.

In at least another aspect at of least one embodiment of the present disclosure, the one or more signals are derived from waveforms having one or more features selected from the group of: variable intervals between successive stimulation events, variable pulse separation, the interval between one or more of the stimulation events local peaks of the one or more signals provided to the mammal have a duration of approximately 10 nanoseconds to one second during a one-second treatment interval, and is modulated using aperiodic continuous waveform functions or particular pulse separation intervals.

In at least another aspect at of least one embodiment of the present disclosure, the one or more signals also have at least two stimulation events delivered within a time interval of about 10 nanoseconds to 100 seconds.

In at least another aspect at of least one embodiment of the present disclosure, the one or more signals are nonrepeating within a time interval between about 10 nanoseconds to 100 seconds.

In at least another aspect at of least one embodiment of the present disclosure, the one or more signals delivers at least 400 stimulation events in a 1-second interval.

In at least another aspect at of least one embodiment of the present disclosure, the one or more signals provides eight stimulation events of 2 msec pulse duration at approximately 63.89 msec, 183.79 msec, 337.98 msec, 457.82 msec, 550.91 msec, 653.69 msec, 878.31 msec and 970.20 msec within the 1st second of the one or more signals provided.

In at least another aspect at of least one embodiment of the present disclosure, the one or more signals also have one or more features selected from the group of: a variable local peak level, a non-constant repetition frequency, variable intervals between successive stimulation events or variable pulse separation.

In at least another aspect at of least one embodiment of the present disclosure, the one or more signals are derived from waveforms having one or more features selected from the group of: variable complexity, variable frequency content and variable bandwidth.

In at least another aspect at of least one embodiment of the present disclosure, the one or more signals also have features selected from the group of: the interval between one or more of the stimulation events local peaks of the one or more signals provided to the mammal have a duration of approximately 10 nanoseconds to one second during a one-second treatment interval, the one or more signals generated is modulated using aperiodic continuous waveform functions and/or particular pulse separation intervals, the one or more signals have at least two stimulation events delivered within a time interval of about 10 nanoseconds to 100 seconds or the one or more signals are nonrepeating within a time interval between about 10 nanoseconds to 100 seconds.

In at least another aspect at of least one embodiment of the present disclosure, the one or more signals delivers at least 400 stimulation events in a 1-second interval.

In at least another aspect at of least one embodiment of the present disclosure, the one or more signals also have at least three stimulation events delivered within about 10 nanoseconds to 100 seconds with different time intervals between each of the components of the one or more signals.

In at least another aspect at of least one embodiment of the present disclosure, the one or more signals also have at least three stimulation events delivered within about 1 second with different time intervals between each of the components.

In at least another aspect at of least one embodiment of the present disclosure, the one or more signals are nonrepeating within a time interval for the one or more signals between about 10 nanoseconds to 100 seconds.

In at least another aspect at of least one embodiment of the present disclosure, a device for increasing heat shock protein expression in a mammal is provided. The device comprises a power supply, an amplifier, an antenna and a waveform generator where the amplifier is an A-class linear or E-class low-power operating in the frequency range from $\frac{1}{100}$th Hz to 100 GHz.

In at least another aspect at of least one embodiment of the present disclosure, a device for increasing heat shock protein expression in a mammal is provided. The device comprises a power supply, an amplifier, an antenna and a waveform generator configured to deliver light waves in the infrared, visible and ultraviolet frequency ranges.

In at least another aspect at of least one embodiment of the present disclosure, a device for increasing heat shock protein expression in a mammal is provided. The device comprises a power supply, an amplifier, an antenna and a waveform generator configured to deliver mechanical vibrations in the frequency range from $\frac{1}{100}^{th}$ of a Hz to 30,000 Hz.

In at least another aspect at of least one embodiment of the present disclosure, a device for increasing heat shock protein expression in a mammal is provided. The device comprises a power supply, an amplifier, an antenna, a battery and a waveform generator where the device is battery powered.

In at least another aspect at of least one embodiment of the present disclosure, a device for increasing heat shock protein expression in a mammal is provided. The device comprises a power supply, an amplifier, an antenna and a waveform generator, where the device is wearable.

In at least another aspect at of least one embodiment of the present disclosure, a device for increasing heat shock protein expression in a mammal is provided. The device comprises a power supply, an amplifier, an antenna and a waveform generator, where the power supply is wireless.

In at least another aspect at of least one of the present disclosure, a device for increasing heat shock protein expression in a mammal is provided. The device comprises a power supply, an amplifier, an antenna and a waveform generator, where the waveform generator is analog or digital operating from $\frac{1}{100}^{th}$ Hz to 100 MHz.

In at least another aspect at of least one of the present disclosure, a device for increasing heat shock protein expression in a mammal is provided. The device comprises a power supply, an amplifier, an antenna and a waveform generator, where the waveform generator is analog or digital operating in FCC-allocated Industrial Scientific and Medical (ISM) bands centered around 6.78, 13.56, 27.12 and 40.68 MHz.

In at least another aspect at of least one embodiment of the present disclosure, a device for increasing heat shock protein expression in a mammal is provided. The device comprises a power supply, an amplifier, an antenna and a waveform generator, where the waveform generator uses a digital synthesis module or crystal oscillator operating at 27.12 MHz.

DRAWINGS

FIG. 1 shows table of various signal parameters that were used in the study disclosed herein.

FIGS. 7-18 show data tables showing local peak locations, peak amplitudes, and pulse durations for a "Class R" waveform.

FIGS. 19-25 show data tables showing local peak locations, peak amplitudes, and pulse durations for a "Class A" waveform.

Figure 27:
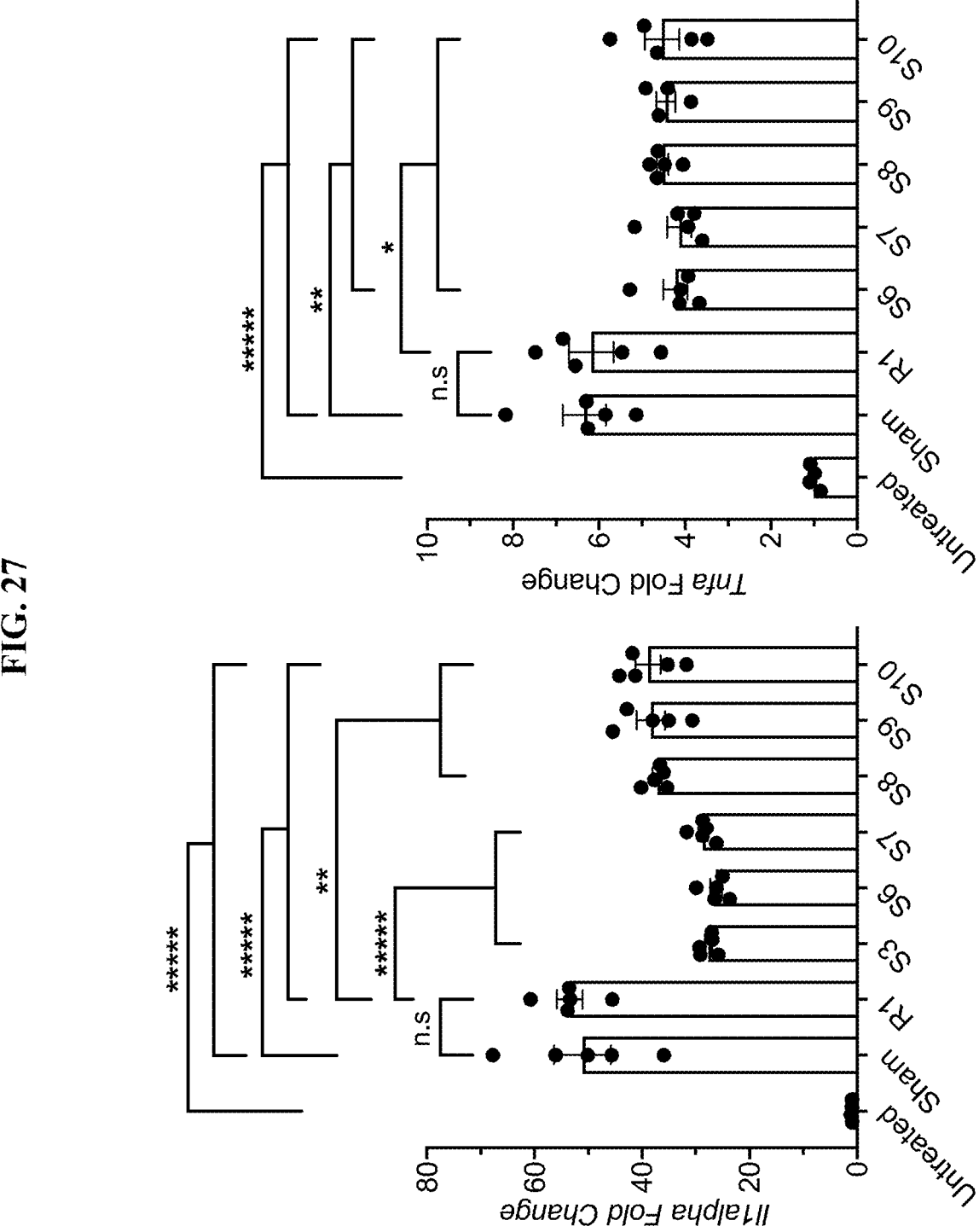

FIG. 27 shows data from a second series of experiments: As demonstrated by the results shown, all new signals tested produced significantly greater reductions in IL-1a, TNF-a pro-inflammatory cytokines and inflammation as compared to the Reference Signal R1. Here, the Reference Signal R1 was unable to produce a significant effect on cytokine expression, whilst all of the new signals were able to do so.

Figure 28:
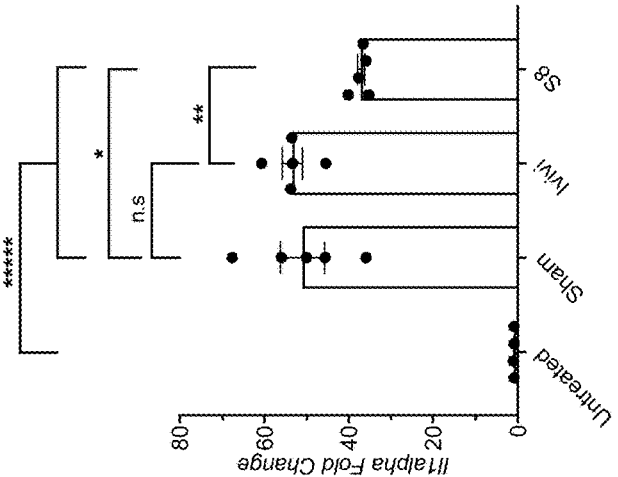
Figure 28:
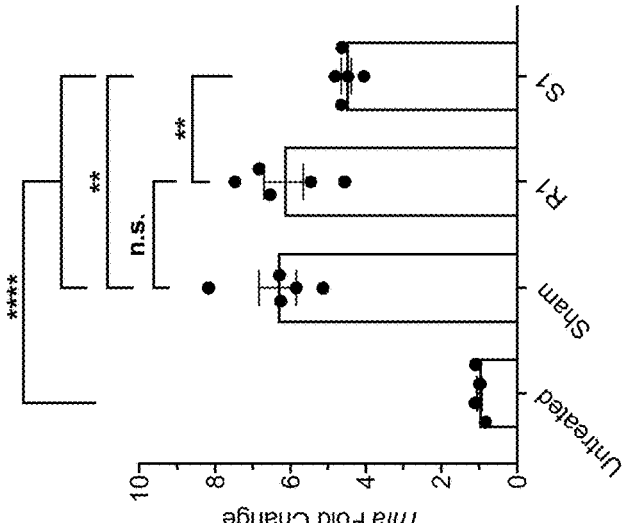
Figure 28:
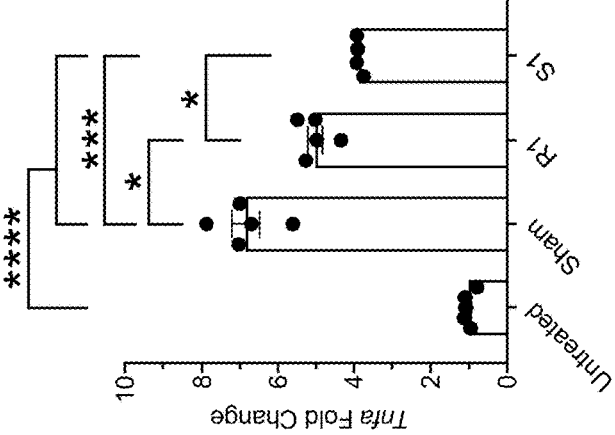

FIG. 28 shows waveform dependence of new signals from two independent experiments: Left: data from $1^{st}$ series of experiments (FIG. 26) showing Signal S1 produced greater reduction in pro-inflammatory cytokine TNF-a compared to Reference Signal R1. Middle: data from a second series of experiments (FIG. 27) showing Signal S1 produced greater reduction in pro-inflammatory cytokine TNF-a compared to Reference Signal R1. Right: data from a second series of experiments (FIG. 27) showing Signal S8 produced greater reduction in pro-inflammatory cytokine TNF-a compared to Reference Signal R1. Notably, all signals in these experiments have the same 5 μT peak amplitude, demonstrating that waveform features of the new signals are responsible for greater reductions in TNF-a.

Figure 29:
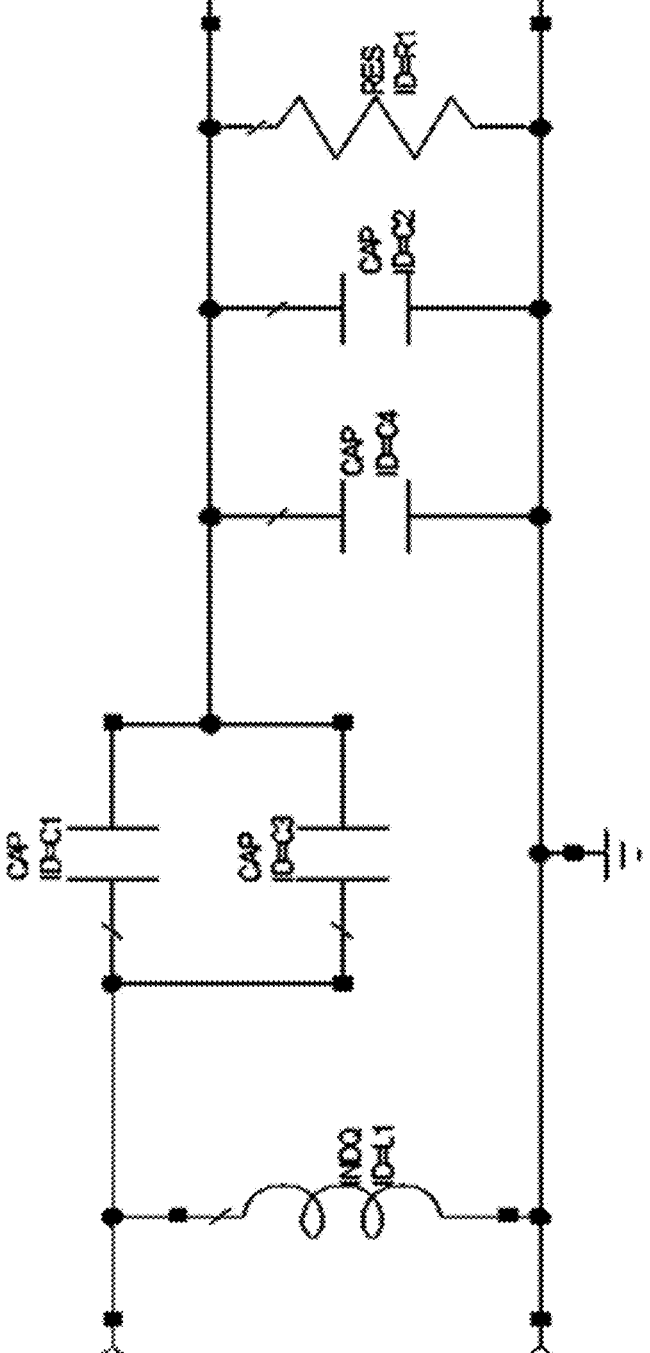

FIG. 29 shows schematic diagram of Antenna Matching Circuit.

Figure 30:

FIG. 30 shows oscilloscope trace of Signal S2, using "Class R" waveform with 27.12 MHz carrier frequency at peak amplitude=10 μT, corresponding to 312 mV peak-to-peak on Beehive probe.

Figure 31:
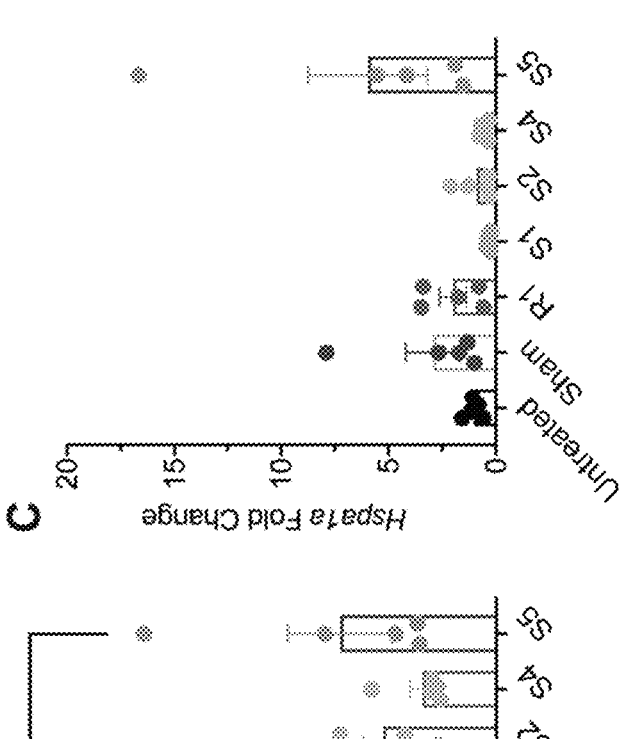
Figure 31:
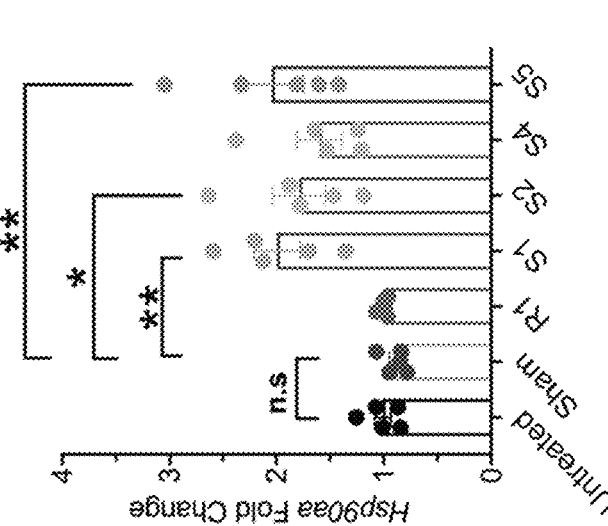

FIG. 31 shows the results demonstrating PEMF stimulation increases gene expression of heat shock proteins in BV2 cells. A.-C. qPCR analysis of pro-inflammatory cytokine gene expression (Hsp90aa, Hspd1, and Hspa1a) in BV2 cells pre-treated with LPS and stimulated with PEMF signals (Ref, S1, S2, S4 and S5). Data displayed as mean+SEM, one-way ANOVA with Dunnett's multiple comparison test, $*p<0.05$, $p<0.01$, $*p<0.005$, n=5.

DEFINITIONS

For purposes of the present disclosure, the indicated terms shall be defined as follows:

aperiodic continuous waveform function: A continuous waveform possessing three or more peaks with unequal pulse separations during an interval.

aperiodic pulse train: A nonrepeating sequence of rectangular pulse waveforms. Unless otherwise specified, none of the pulse waveforms in the sequence are assumed to be identical.

continuous waveform: a waveform with amplitude level A(t) dependent upon time t, such that arbitrarily small changes in amplitude level $|A(ti)-A(tj)| < \Delta A$ can be assured for sufficiently small changes in time $\Delta t = |ti-tj|$, where $ti \neq tj$.

duty factor: for a periodic pulse train, the ratio of the pulse duration to the waveform period.

half-height interval: the interval t2–t1 between the two instants t1 and t2 such that t2>t1 and A(t1)=A(t2)=50%*A (tp)/100, where A(tp) is the level of a local peak occurring at time t=tp, and there exists exactly one tp where t1<tp<t2 and waveform level A(tp) is a local peak.

half-height level (stimulation duration): the value of 50%*A(tp)/100, where A(tp) is the level of a local peak occurring at time t=tp.

interval: The difference in continuous time between two instants t1 and t2.

level, continuous waveform: the value of a waveform specified at every time t within a given interval.

level, rms: for a digitally sampled waveform takes on n discrete values $A_j$, all equally spaced in time, the rms level is given by $$\text{rms} = \sqrt{\frac{1}{n}\sum_{i=1}^{1=n} A_i^2}.$$

level: the value of a waveform having the same units as A(t).

non-constant repetition frequency: Having three or more peaks with unequal pulse durations during an interval.

peak, local (continuous waveform): A(tp) is a local peak if there is an interval (t1,t2) with t1<tp<t2 and A(tp)>A(t) for every tin (a,b).

peak, local (sampled waveform): a waveform data sample A(t$_i$) with level larger than its two neighboring samples.

peak: pertaining to the greatest value of the waveform across a specified interval.

periodic (aperiodic): Having the properties of a periodic (aperiodic) function f(t) such that there exists a constant T>0 such that f(t+T)=f(t).

periodic pulse train: a repetitive sequence of rectangular pulse waveforms. Unless otherwise specified, all of the pulse waveforms in the sequence are assumed to be identical.

pulse duration: equivalent to half-height interval.

pulse separation: the interval between two successive local peaks.

pulse waveform: a waveform consisting of one or more pulses.

pulse: a region of a waveform defined by a local peak with nonzero pulse duration.

reference: of or pertaining to a time, level, waveform feature, or waveform that is used for comparison with, or evaluation of, other times, levels, waveform features, or waveforms.

repetition frequency: the value of the reciprocal of the pulse separation.

repetitive: Of or pertaining to a series of specified waveform features or waveforms that repeat or recur (do not repeat or recur) in time.

signal feature: A specified portion or segment of a signal determined by a waveform feature.

signal: a physical phenomenon that is a function of time and space.

stimulation duration: half height interval.

stimulation event: occurrence of a local waveform peak with amplitude >5% peak value of the waveform across a specified interval.

variable intervals: Having two or more intervals of unequal duration between successive pulses during an interval.

variable local peak level: Having non-constant peak level over an interval.

waveform feature: A specified portion or segment of a waveform.

waveform feature: a specified portion or segment of a waveform.

waveform period: The minimum duration after which a periodic waveform repeats.

waveform, sampled, periodically: A finite sequence of levels y0, y1, y2, . . . , yn each of which represents the value of the waveform at times t0, t0+$\Delta$t, t0+2$\Delta$t, . . . , t0+n$\Delta$t, respectively, wherein the data may exist in a pictorial format or as a list or table of numbers.

waveform: a representation of a signal (for example, a graph, plot, oscilloscope presentation, discrete time series, equations, or table of values). This term refers to a measured or otherwise-defined estimate of the physical phenomenon or signal.

DETAILED DESCRIPTION

In the experiments shown and described herein, a BV-2 mouse microglial cell culture model for inflammation cell was chosen to test the ability of different PRF signals to reduce pro-inflammatory cytokine and thus reduce inflammation. Cytokines are proteins released by cells that have specific effects on the interactions and communications between cells (Zhang 2007). Inflammatory cytokines regulate inflammation by directing both the immune cell activity and intracellular signaling control mechanisms that characterize inflammation (Turner 2014). Pro-inflammatory cytokines increase inflammation: increases in pro-inflammatory cytokines increase the expression of corresponding genes directing cells to increase inflammation via autocrine, paracrine, and endocrine functions (Turner 2014, Garth 2018), causing both the clinical diagnostic symptoms of acute inflammation and often-undiagnosed chronic inflammation (Ferrero-Miliani 2007, Garth, 2018).

Pro-inflammatory cytokines IL-1 IL1-1$\alpha$, IL-1$\beta$), Il-6, and TNF (TNF-$\alpha$, TNF-$\beta$) produce inflammation responsible for a wide variety inflammatory diseases (Zhang 2007, Cavalli 2012, Gao 2010, Kany 2019).

Cell Culture Model: BV-2 microglia were plated at a density of 200,000 cells/well in in 6-well culture dishes (Sigma Aldrich, NACRES NB.22). Twenty-four hours later, cells were treated with 30 ng/ml of lipopolysaccharide (LPS) (Sigma Aldrich MFCD00164401) (total volume of 1 ml), then immediately placed in the incubator for PRF or sham treatment. After stimulation, cells were placed in a dedicated incubator with $CO_2$ and temperature controlled to $\pm 1\%$ (model 3158; Forma, Marietta, OH). Twenty-four hours later, cell culture supernatant was collected, and 1 ml of TRIzol reagent (Thermo Fisher Scientific, Cat. #. 15596026) was added to the cells. Cell lysates in TRIzol were either frozen at −80 degrees Celsius or processed immediately for RNA isolation. Cells were homogenized in TRIzol (Sigma Aldrich MFCD00213058) by scraping and pipetting up and down with a pipet tip. Samples were transferred into new 2 ml Eppendorf tubes (Sigma Aldrich Z628034-500EA) and incubated at room temperature for 5 minutes. 0.2 ml of Chloroform (Sigma Aldrich C2432) was added to each tube, and tubes were shaken vigorously for 15 seconds with the cap closed. Samples were incubated at room temperature for 3 minutes, then centrifuged at 12,000 g for 15 minutes at room temperature. The aqueous phase of the sample was transferred into a new 2 ml Eppendorf tube, and 1 ml of 100% isopropanol (Sigma Aldrich W292907) was added to precipitate the RNA. The samples were incubated at room temperature for 10 minutes and centrifuged at 12,000 g for 15 minutes at room temperature. Supernatant was discarded, and 1 ml of 75% Ethanol (Sigma Aldrich 459836) was added to each tube. Sample was briefly vortexed and centrifuged at 7,500 g for 5 minutes at room temperature. Supernatant was discarded, and RNA pellet was dried for 15 minutes with the tube cap open at room temperature. RNA was re-suspended with 20 ul of RNase-free water using a pipette tip to mix up and down. Tubes were incubated in a heat block at 55 degrees for 10-15 minutes to aid the resuspension. RNA concentration was measured using Nanodrop (ThermoFisher Scientific, Cat. #. 840-329700): RNA samples were diluted to 100 ng/ul. cDNA was synthesized using ABI hiCapacity cDNA Reverse Transcriptase kit (Thermo Fisher Scientific, Cat. #. 4368813): each reaction (a total volume of 100 ul) was comprised of 50 ul of the master mix (10 ul of 10×RT Buffer, 4 ul of 100 mM dNTP mix, 10 ul of 10×RT random primers, 5 ul of 50 U/ul Multiscribe Reverse Transcriptase, and 21 ul of RNase-free dH$_2$O), 30 ul of RNase-free dH$_2$O, and 20 ul of 100 ng/ul RNA sample. Each reaction was mixed in a labeled 0.2 ml PCR tube (ThermoFisher Scientific, Cat. #. AB0620G). PCR tubes were placed in a Thermal Cycler (Sigma Aldrich Z739472), and cDNA was synthesized using a two-step method (Step 1: 25 degrees for 10 minutes; Step 2: 37 degrees for 120 minutes). qPCR was run in a 96-well plate (MicroAmp™ Fast Optical 96-Well Reaction Plate, 0.1 mL, Thermo Fisher Scientific, Cat. #. 4346907) with StepOnePlus™ Real-Time PCR System (Thermo Fisher Scientific). Each reaction (total volume of 25 ul) was comprised of 12.5 ul of Taqman Master Mix (Thermo Fisher Scientific, Cat. #. 4364340), 1.25 ul of corresponding gene expression assay (Thermo Fisher Scientific, Cat. #. 4331182), 8.75 ul of RNase-free H2O, and 2.5 ul of cDNA sample. GAPDH (Thermo Fisher Scientific, Cat. #. 4352339) was used as a housekeeping gene for normalization. Taqman gene expression assays for mouse IL-1α (Mm00439620_m1), IL-1β (Mm00434228_m1), IL-6 (Mm00446190_m1), TNF-α (Mm00443258_m1), Hsp90aa (Mm00658568_gH), Hspd1 (Mm00849835_g1), and Hspa1a (Mm01159846) were purchased from Thermo Fisher Scientific. Each sample was run in triplicate. When possible, all samples were fit into one 96-well plate for one gene of interest. 96-well plate was then spun at 2,000 RPM for 2 minutes at 4 degrees and loaded to StepOnePlus® Real-Time PCR System and run using the Comparative $C_T$ ($\Delta\Delta C_T$) method. Comparative $C_T$ ($\Delta\Delta C_T$) method was used to quantify the relative gene expression levels in each sample. Statistical analyses were performed using GraphPad Prism ver. 9.0 (GraphPad Software, San Diego, CA). Comparisons between the two groups were done via unpaired t-test; comparisons between multiple treatment groups were done via one-way or two-way analysis of variance (ANOVA) with indicated multiple comparisons post hoc tests.

PRF Delivery to Cell Cultures: eleven different nonthermal PRF signals consisting of a Reference Signal R1 and ten new signals S1-S10 were delivered to BV-2 mouse microglial cells using a tuned single-turn 20-cm diameter coil antenna resting horizontally in the plane of a plastic shelf in a dedicated cell culture incubator with CO2 and temperature controlled to ±1% (model 3158; Forma, Marietta, OH). The antenna consisted of a single turn of solid copper wire of 14 AWG (Digikey, part number A541401B-100-ND) soldered onto a custom-made matching circuit configured according the to schematic shown in FIG. 29. The efficiency of the coil applicator was maximized for each of the radiofrequencies employed here through the use of a custom-made tunable matching circuit. The matching circuit consisted of: L1 (Digikey 445-1540-1-ND 22 uF Inductor) used only for DC path to help the amplifier detect that a coil is connected; C1 and C2 (Digikey 338-4113-ND 5 pF 1210) are 500V Mica Chip matching caps; C3 and C4 are tunable Trimmer Caps (Digikey 1674-1053-ND, Trimmer 1.5-40 pF). All four capacitances (C1-C4) had the same minimum breakdown-voltage specifications >1 kV. The locus size of the tuning is determined by the value of C3 such that a larger locus size reduces the coil tuning center frequency. The capacitance C4 was then adjusted to tune to the center frequency, optimizing field strength delivered. The center frequency can also be tuned by adjusting coil L1.

The PRF signals were generated from waveforms digitally sampled at 100 kHz using a signal generator (model SDG2082X, Siglent, Solon, Ohio), and amplified using a high-precision linear radiofrequency power amplifier (model 150A100, Amplifier Research, Souderton PA) with amplifier output connected to the RF input on the coil matching circuit. All cabling and connectors were appropriately shielded to obviate losses in signal strength and fidelity.

PRF signal strengths and waveform integrity were assessed and verified for each experiment using a calibrated shielded loop probe 1 cm in diameter (model 100A; Beehive Electronics, Sebastopol, CA) connected to a calibrated 100-MHz oscilloscope (model DS1202; Rigol, Beaverton, OR) using a 50-Ohm terminator rated at 2% accuracy (Digikey 501-1036-ND) to ensure accurate calibration with the Beehive probe and oscilloscope. The oscilloscope trace of exemplar waveform S1 as delivered for the experiments is shown in FIG. 30. To minimize pre-antenna losses due to unbalanced currents flowing on the antenna cable, it is necessary to place a ferrite choke balun between the cable and the antenna feed. In the absence of a balun, the measured antenna impedance becomes overly sensitive to the configuration of the feed cable. The RF input cable (Digikey RG14, Amphenol RF 135110-07-24.00) was equipped with 14 clip-on ferrite choke balun elements (Digikey 399-10836-ND, KEMET ESD-SR-12). Total cable length was 24 inch/60 cm using SMA-Male to SMA-Female connectors (Digikey). The choke is extremely broad-band and has a Rejection Impedance of approximately 1000 Ohms from bands 160 m-2 m, was wrapped in weather-proof shrink-tubing (Qualtek Q5-3X-3/16-01-QB48IN-25) and had PL259 Male-Connectors (Digikey 1837-PL259-ND) on each side.

The apparatus delivered to cell cultures 11 PRF signals with peak field strengths ranging from 2-15 μT: 10 new signals (S1-S10) and a Reference Signal (R1). Waveform parameters for all signals are shown in FIG. 1, Table of Signal Parameters. Signals S1-S10 were compared to an FDA-cleared Reference Signal R1. Waveform parameters are shown in the Table of Signal Parameters, FIG. 1. Exemplar waveforms for Signals S1-S10 are shown in FIGS. 2-7.

The R1 reference signal, consisting of a rectangular burst of 27.12 MHz sine waves, repeating at 2 bursts/sec and transmitted with 5 µT peak magnetic field strength, was chosen for the substantial and consistent evidence for efficacy in cell models, animal models for edema (Johnson 2006), angiogenesis (Roland 2000, Weber 2004,) and tissue repair (Strauch 2006, Callahan 2007, Patel 2008) and human clinical studies showing); and human clinical trials showing significant reductions in pain (Heden 2008, Rohde 2010, 2015), decreased use of pain medication and inflammatory cytokine reduction (Rohde 2010, 2013, 2015).

Figure 2:
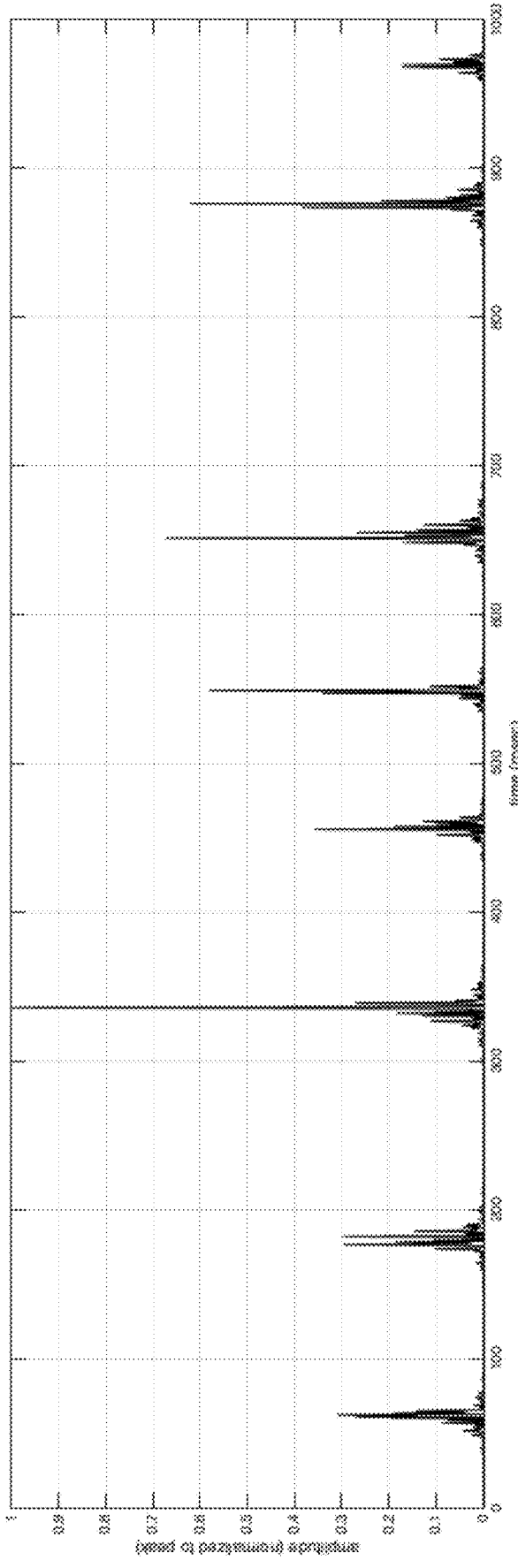
FIG. 2 shows 1-second duration of "Class R" waveform employed for signals S1-S3 in this study.
Figure 3:
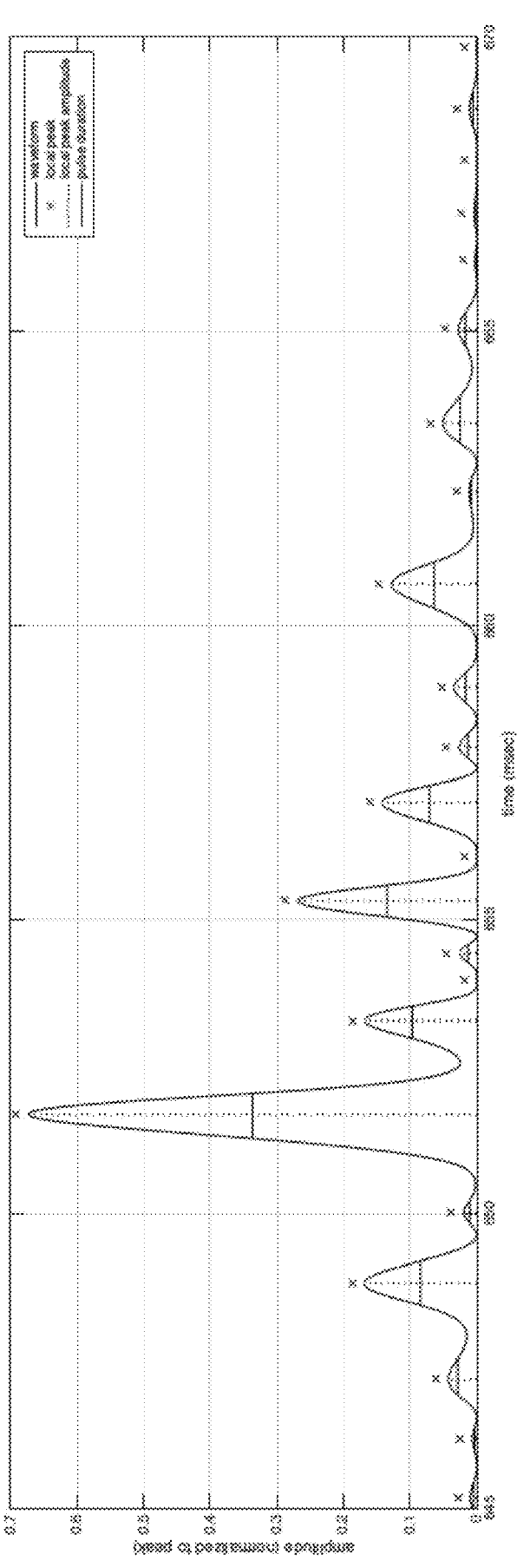
FIG. 3 shows 25 msec duration of "Class R" waveform in FIG. 2.

All "Class R" Signals S1-S3 used in this study were formed using the "Class R" waveform shown in FIG. 2 to amplitude modulate a 27.12 MHz sinusoidal wave with peak amplitudes according to the Table of Signal Parameters shown in FIG. 1. FIG. 2 shows 1-second duration of "Class R" waveform employed for Signals S1-S3 in this study, and FIG. 3 shows a 25 msec portion of the "Class R" waveform, illustrating local peak locations, peak amplitudes, and pulse durations, all amplitudes normalized to peak waveform level. The "Class R" waveform is an aperiodic continuous function with 911 local peaks occurring in the $1^{st}$ second, with rms level=0.0313 during this interval. FIGS. 7-18 show a table of peak locations, local peak amplitudes, and pulse durations for the "Class R" waveform.

Figure 4:
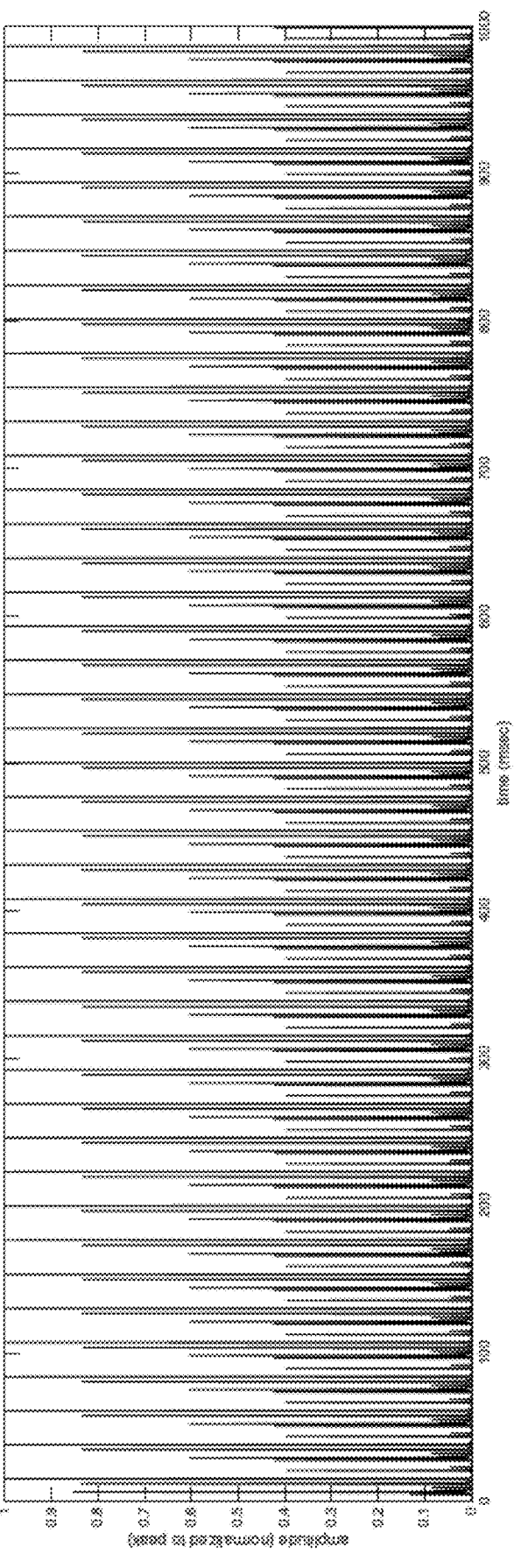
FIG. 4 shows 1-second duration of "Class A" waveform employed for signals S4-S7 in this study.
Figure 5:
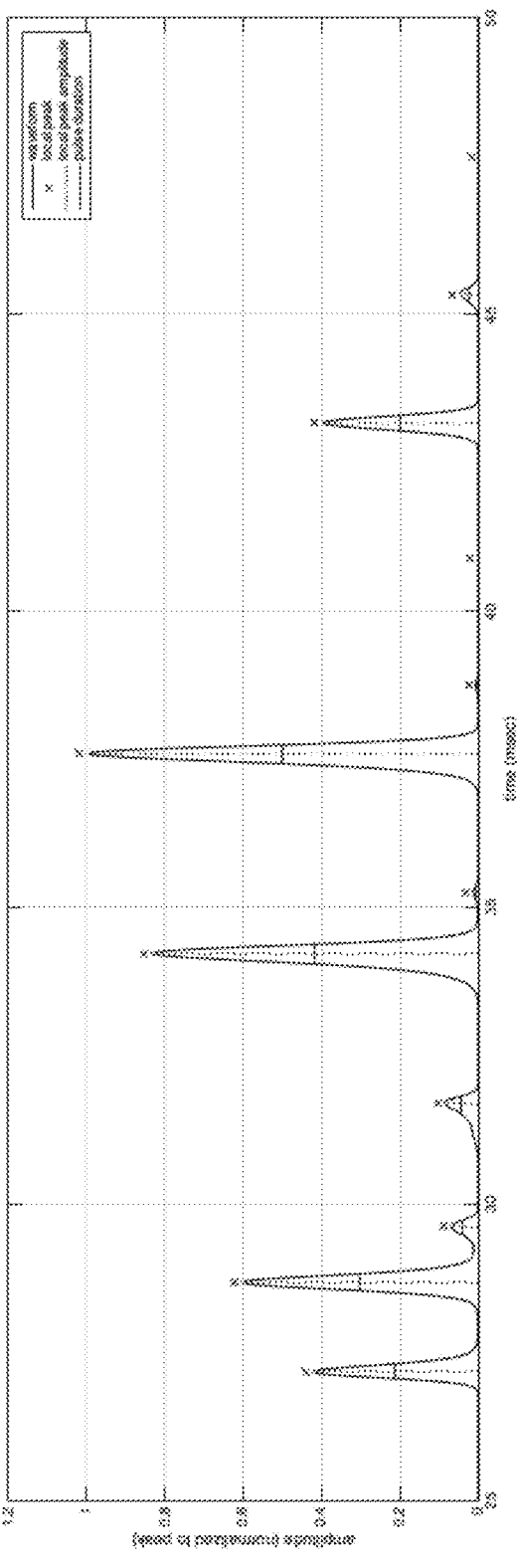
FIG. 5 shows 25 msec duration of signal in FIG. 2.

All "Class A" Signals S4-S7 used in this study were formed using the "Class A" waveform shown in FIG. 4 to amplitude modulate a 27.12 MHz sinusoidal wave with peak amplitudes according to the Table of Signal Parameters shown in FIG. 1. FIG. 4 shows 1-second duration of "Class A" waveform employed for Signals S4-S7 in this study, and FIG. 5 shows a 25 msec portion of the "Class A" waveform, illustrating local peak locations, local peak amplitudes, and pulse durations, all amplitudes normalized to peak waveform level. The "Class A" waveform is an aperiodic continuous function with 518 local peaks occurring in the $1^{st}$ second, with rms level=0.1101 during this interval. FIGS. 19-25 show a table of peak locations, local peak amplitudes, and pulse durations for the "Class A" waveform.

Figure 6:
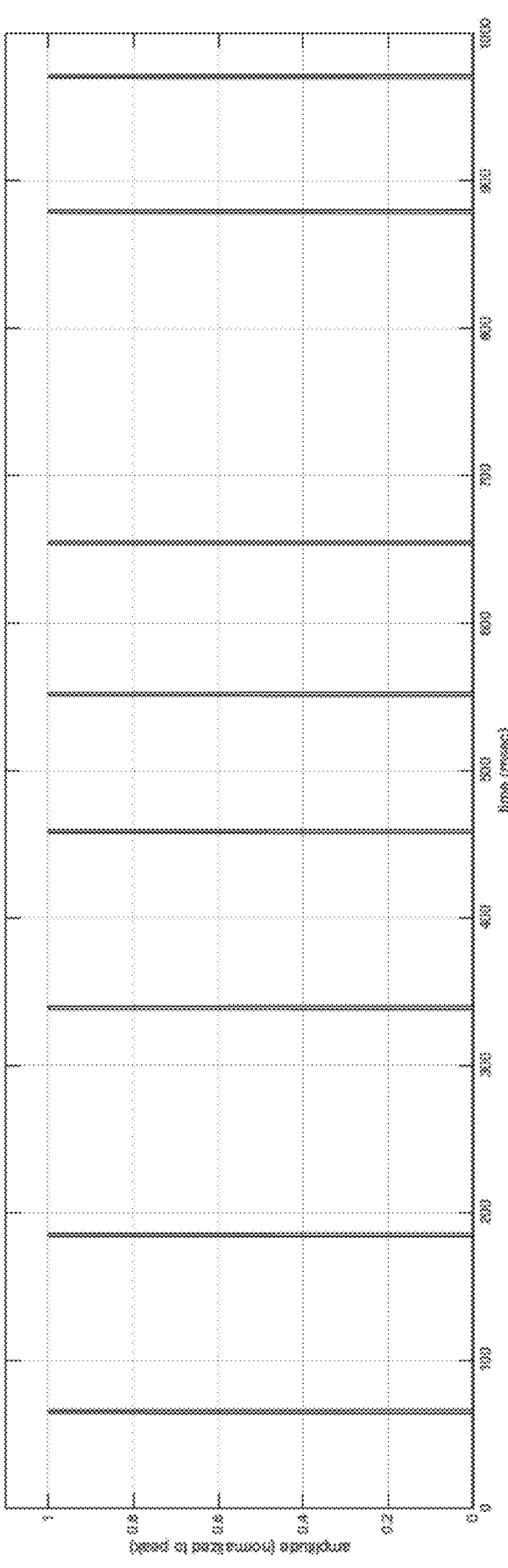
FIG. 6 shows 1-second duration of a "Class DR" waveform for employed for signals S8-S10 in this study.

All "Class DR" signals S8-S10 were formed using the "Class DR" waveform shown in FIG. 6 to amplitude modulate a 27.12 MHz sinusoidal wave with peak amplitudes according to the Table of Signal Parameters shown in FIG. 1. FIG. 6 shows 1-second duration of "Class DR" waveform employed for Signals S8-S10 in this study. The "Class DR" waveform is an aperiodic pulse train with 8 pulses occurring in the $1^{st}$ second, with duty factor=0.016 during this interval. The "Class DR" waveform consists of an aperiodic pulse train, with pulse duration=2 msec for all pulses, and first instants of pulses located at 63.89 msec, 183.79 msec, 337.98 msec, 457.82 msec, 550.91 msec, 653.69 msec, 878.31 msec and 970.20 msec within the $1^{st}$ second of the signal.

The waveforms employed for Signals S1-S10 differ from the Reference Signal R1 in their construction and thus the type of stimulation delivered to the biological target: the Reference Signal R1 consists of a periodic pulse train consisting of 27.12 MHz sine waves of constant amplitude=5 µT; constant pulse duration=2 msec, separated in time by a fixed interval of 500 msec, producing equal pulse separation between adjacent pulses. While convenient for use in low-cost disposable signal delivery devices, the use of a periodic pulse trains results in a constant rate of stimulation, with equal intervals between successive stimulation events (pulse separation), and no variability in stimulation level (amplitude), stimulation duration (pulse duration), signal spectrum, or any other waveform features.

In contrast, none of the 10 new signals S1-S10 consists of periodic pulse trains: All "Class R" and "Class A" signals S1-S7 are derived from aperiodic continuous waveforms consisting of amplitude-modulated 27.12 MHz sine waves, where the modulation waveforms are shown in FIGS. 2-5. While requiring high-precision linear amplifiers with appropriate power supplies to deliver the signals to the biological target, all "Class R" and Class A" signals deliver a calibrated non-constant rate of stimulation, with variable intervals between successive stimulation events (pulse separation), and variability in stimulation level (amplitude), stimulation duration (pulse duration), repetition frequency, signal spectrum and all other waveform features. All "Class DR" signals S8-S10 are derived from aperiodic pulse trains, delivering a calibrated non-constant rate of stimulation, with variable intervals between successive stimulation events (pulse separation), and variability in stimulation duration (pulse duration), signal spectrum, and all other waveform features determined by pulse duration and pulse separation.

PRF Treatments: PRF treatments were delivered by placing the coil antenna resting horizontally in the plane of a plastic shelf in a dedicated incubator with CO2 and temperature controlled to ±1% (model 3158; Forma, Marietta, OH). Culture dishes were placed in the central portion of the coil at 2-6 cm from the perimeter. Sham treatments were performed with the PRF delivery apparatus remaining in the cell culture incubator with all power supplies to the antenna switched off. Untreated samples with no LPS stimulation were run for each series of experiments in order to assess the effect of LPS stimulation. After 15 minutes of PRF or sham treatment, coils were deactivated and cells remained in the cell culture incubator for 24 hrs, at which time the cells and supernatant were gathered for analysis, and the latter analyzed using a Life Technologies cytokine multiplex kit (model 30, Fisher Scientific). Fold-changes for cytokine expression were analyzed using unpaired 2-tailed t-tests using Prism software (GraphPad Software, San Diego, CA). All experiments were repeated 5 times.

In at least some of the embodiments of the present disclosure, the signal effect sizes varied with peak magnetic field strength and waveshape, showing that new signals can be configured by varying signal parameters to produce greater efficacy than previous FDA-cleared signals. A neuronal cell culture model of neuroinflammation and regeneration/repair/regrowth was employed to evaluate the anti-inflammatory and regenerative properties of eleven different pulsed radiofrequency signal variants, including 10 newly developed signals intended for therapeutic uses and one FDA-cleared signal in current clinical use.

Results

Figure 26:
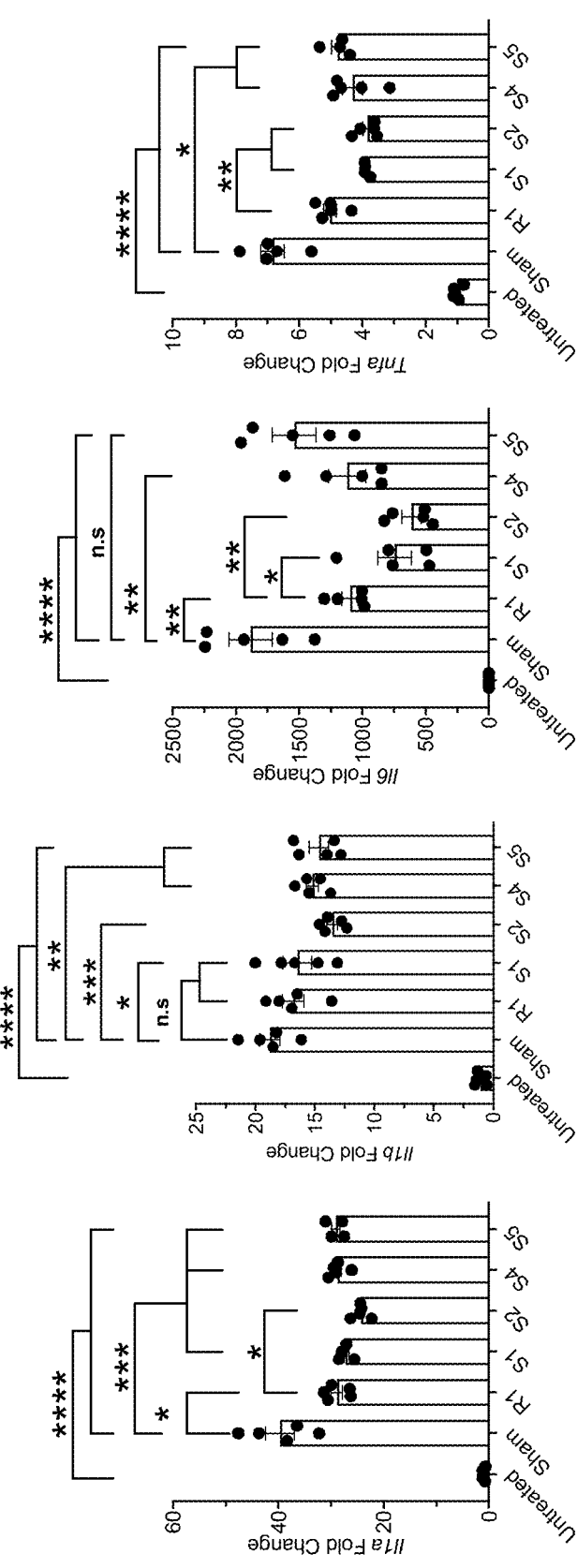
FIG. 26 shows data from $1^{st}$ series of experiments: Signals S1, S2, S4 and S5 significantly reduced IL-1a, TNF-a and IL-6 pro-inflammatory cytokine expression in a mouse BV2 microglial cell model for inflammation using 30 ng/ml LPS stimulation. Signals S1 and S2 showed significantly greater reductions in IL-1a, TNF-a and IL-6 pro-inflammatory cytokines compared to the Reference signal R1.

Stimulation of BV-2 microglial cells with 30 ng/ml LPS induced significant upregulation compared to untreated cells for all pro-inflammatory cytokines tested: IL1-1α, IL-1β, Il-6 and TNF-α (FIGS. 26-27). Two series of experiments were performed, in which all ten new PRF signals produced significant reductions compared to sham in IL1-1α, IL-1β, Il-6 and TNF-α pro-inflammatory cytokine expression and therefore inflammation in a mouse BV-2 microglial cell model (FIGS. 26-27). The Reference Signal R1 produced significant reductions in IL1-1α, IL-1β, Il-6 and TNF-α pro-inflammatory cytokines in the first series of experiments (FIG. 26), but was unable to produce significant reductions in these cytokines in a second series of experiments (FIG. 27).

A first series of experiments compared new PRF Signals S1, S2, S4 and S5 to the Reference Signal R1 (FIG. 26), showed that Signals S1 and S2 produced significantly greater reductions compared to the Reference signal R1 in IL-6 ($2^{nd}$ plot from right) and TNF-a (right-hand plot) pro-inflammatory cytokines. Signal S2 also produced significantly greater reductions compared to the Reference signal R1 in pro-inflammatory cytokine IL-1a (left-hand plot).

A second series of experiments compared new PRF Signals S3, S6, S7, S8, S9 and S10 to the Reference Signal R1, with all of these new PRF Signals S1 and S2 producing significantly greater reductions in IL-1a and TNF-a pro-inflammatory cytokines compared to the Reference signal R1 (FIG. 27, left-hand and right-hand plots). Notably, in the second series of experiments, conducted under the same experimental conditions as the previous series, the Reference Signal R1 was unable to produce a significant effect on cytokine expression, whilst all of the new PRF signals were able to do so, demonstrating the superiority of the new PRF signals for reducing pro-inflammatory cytokine expression.

The results of these experiments show that new PRF signals S1-3 and S6-S10 consistently outperformed the Reference Signal S1 (FIGS. 26-27), producing significantly greater reductions in pro-inflammatory cytokine expression compared to the Reference Signal R1: Signals S2-S3 and S6-S10 produced significantly greater reductions in IL-1a (FIGS. 26-27, left-hand plots); New signals S1, S2 and S6-S10 produced significantly greater reductions in TNF-a (FIGS. 26-27, left-hand plots). Additionally, new Signal S2 produced significantly greater reductions in Il-1b (FIG. 26, $2^{nd}$ plot from left);

Notably, FIG. 28 shows that two of the new PRF signals, each with 5 μT peak amplitude, produced significantly greater reductions in pro-inflammatory cytokines expression compared to the Reference Signal R1 in two independent experiments. Left hand plot: data from first series of experiments (FIG. 26) showing Signal S1 produced greater reduction in pro-inflammatory cytokine TNF-a compared to Reference Signal R1. Middle plot: data from second series of experiments (FIG. 27) showing Signal S1 produced greater reduction in pro-inflammatory cytokine TNF-a compared to Reference Signal R1. Right hand plot: data from second series of experiments showing Signal S8 produced greater reduction in pro-inflammatory cytokine IL-1a compared to Reference Signal R1. Notably, all signals, including the Reference Signal R1, in these three experiments have the same 5 μT peak amplitude, demonstrating that differences in waveform features of the new signals S1 and S8 compared to those of the Reference Signal R1 are responsible for greater reductions in TNF-a and IL-1a. New signals S1 and S8 are derived from aperiodic continuous waveform functions (FIG. 2) and aperiodic pulse trains (FIG. 6) These waveforms possess substantially greater complexity, spectral content, temporal variability and potential for information coding compared to the comparatively much simpler repeating pulse train waveform of the Reference Signal R1.

The observation that new signals S1 and S8 produced greater reductions in IL-1a and TNF-a pro-inflammatory cytokine expression compared with the Reference Signal R1 (FIG. 28, left-hand plot), with all signals having peak amplitude=5 μT, shows that new signals can be configured by varying signal parameters to produce greater efficacy than previous FDA-cleared signals.

New PRF signals S1-S10 were all were found to be effective at reducing pro-inflammatory cytokine expression in a mouse BV-2 microglial cell culture model. All of these new signals are derived from aperiodic continuous waveform functions (FIGS. 2-5) and/or aperiodic pulse trains (FIG. 6). These new waveforms have features producing signals with variable complexity, calibrated frequency content, and calibrated corresponding waveform features of the repeating pulse train waveform of the Reference Signal R1. New signals can be configured by varying waveform features to produce greater efficacy compared to previous signals.

The results shown in FIG. 31 demonstrate that PEMF stimulation increases gene expression of heat shock proteins in BV2 cells. A-C. qPCR analysis of pro-inflammatory cytokine gene expression (Hsp90aa, Hspd1, and Hspa1a) was determined in BV2 cells pre-treated with LPS and stimulated with PEMF signals (Ref, S1, S2, S4 and S5). PEMF stimulation restored or even increased the mRNA transcript levels of Hsp90aa and Hspd1, but not that of Hspa1a. Especially the gene expression level of Hspd1 was significantly decreased upon LPS challenge and then increased with PEMF stimulation (FIG. 31). These data suggest that the effect of PEMF stimulation is complex in the context of heat-shock protein expression, the PEMF increases the expression of anti-inflammatory heat shock protein HSP90 and pro-inflammatory cytokine HSP60. Accordingly, the results demonstrate that the PEMF signals tested increase expression of heat shock proteins in a mammal.

It should be appreciated that the embodiments disclosed herein demonstrated, using a neuronal cell culture model of neuroinflammation and regeneration/repair/regrowth, the anti-inflammatory, increasing heat shock protein expression and regenerative properties of 10 newly developed signals intended for therapeutic uses. The signals shown and described herein and claimed as the present invention produced significant increases in heat shock protein expression and reductions in pro-inflammatory cytokine expression in a mouse BV-2 microglial cell model compared to various known signals including but not limited to the indicated FDA-cleared and other known reference signals.

CONCLUSION

Previous work by members of our group, as detailed in the Background, demonstrated that adjustment of the pulse duration and pulse separation of PRF signals of repetitive pulse trains can produce improved efficacy at lower amplitudes. The full range of biological effects due to changes in waveform features remain to be fully elucidated, and remains largely unexplored today. The results of the experiments described here confirmed that greater reductions in pro-inflammatory cytokines in a cell model for inflammation were produced by the new, more complex, highly variable signals S1-S10, as compared to the simpler periodic pulse train of the FDA-cleared Reference Signal R1. All ten new PRF signals S1-S10 produced significant reductions in IL1-1α, IL-1β, Il-6 and TNF-α pro-inflammatory cytokine expression and therefore LPS-induced inflammation in a mouse BV-2 microglial cell model (FIGS. 26-27). Notably, all of these experiments used 30 ng/ml LPS, a comparatively high level of inflammatory activation for the mouse microglial cells used here (Lively, 2018), and under these conditions, the Reference Signal R1 produced small but significant reductions in IL1-1α, IL-1β, Il-6 and TNF-α pro-inflammatory cytokines in the first series of experiments (FIG. 26), but was unable to produce significant reductions in these cytokines in a second series of experiments (FIG. 27).

The first series of experiments compared new PRF Signals S1, S2, S4 and S5 to the Reference Signal R1, with Signals S1 and S2 producing significantly greater reductions in IL-1a, TNF-a and IL-6 pro-inflammatory cytokines compared to the Reference signal R1 (FIG. 26). The second series of experiments compared new PRF Signals S3, S6, S7, S8, S9 and S10 to the Reference Signal R1, with all of these new PRF Signals. Signals S1 and S2 produced significantly greater reductions in IL-1a and TNF-a pro-inflammatory cytokines compared to the Reference signal R1 (FIG. 27).

New PRF signals S1-3 and S6-S10 consistently outperformed the Reference Signal S1 in these experiments, producing significantly greater reductions in pro-inflammatory cytokine expression compared to the Reference Signal S1: Signals S2-S3 and S6-S10 produced significantly greater reductions in IL-1a (FIGS. 26-27); New Signals S1 and S2 produced significantly greater reductions in Il-1b (FIGS. 26-27); New signals S1, S2 and S6-S10 produced significantly greater reductions in TNF-a (FIGS. 26-27).

FIG. 28 shows that two of the new PRF signals, each with 5 µT peak amplitude, produced significantly greater reductions in pro-inflammatory cytokines expression compared to the Reference Signal R1 in two independent experiments. Left hand plot: data from $1^{st}$ series of experiments (FIG. 26) showing Signal S1 produced greater reduction in pro-inflammatory cytokine TNF-a compared to Reference Signal R1. Middle plot: data from second series of experiments (FIG. 27) showing Signal S1 produced greater reduction in pro-inflammatory cytokine TNF-a compared to Reference Signal R1. Right hand plot: data from $2^{nd}$ series of experiments showing Signal S8 produced greater reduction in pro-inflammatory cytokine IL-1a compared to Reference Signal R1. Notably, all signals, including the Reference Signal R1, in these three experiments have the same 5 µT peak amplitude, demonstrating that waveform features of the new signals are responsible for greater reductions in TNF-a and IL-1a.

Waveform features of new signals S1 and S8 are responsible for the significantly greater reductions in pro-inflammatory cytokines expression compared to the Reference Signal R1 shown in FIG. 28. New signals S1 and S8 are derived from aperiodic continuous waveform functions (FIG. 2) and aperiodic pulse trains (FIG. 6). These waveforms possess substantially greater complexity, spectral content, temporal variability and potential for information coding, compared to the comparatively much simpler repeating pulse train waveform of the Reference Signal R1, showing that new signals can be configured by varying waveform features to produce greater efficacy compared to previous FDA-cleared signals.

In this study, we found various types of PEMF stimulation can downregulate the LPS-induced expression and secretion of proinflammatory cytokines, IL-1α, IL-1β, IL-6, and TNF-α, and increase the expression of heat shock proteins in BV2 mouse microglial cells following LPS treatment. PEMF stimulation restored or even increased the mRNA transcript levels of Hsp90aa and Hspd1, but not that of Hspa1a (FIG. 31). New signals S1, S2, S4 and S5 produced significant increases in Hsp90aa while the Reference Signal produced no significant change compared to control (FIG. 31). New Signal S1 Gene expression level of Hspd1 was significantly decreased upon LPS challenge and then increased with stimulation. The data shown and described demonstrates that the effect of PEMF stimulation increases the expression of anti-inflammatory heat shock protein HSP90 and pro-inflammatory cytokine HSP60.

Accordingly, in one embodiment of the present disclosure, a method for reducing inflammation in a mammal is provided. The method includes providing to a mammal in need thereof one or more signals that reduces inflammation in the mammal using a device that generates the one or more signals. The device comprises a power supply, an amplifier, an antenna and a waveform generator where the one or more signals provided has an aperiodic continuous waveform function or an aperiodic pulse train.

In another embodiment of the present disclosure, a method of increasing heat shock protein expression and reducing pro-inflammatory cytokines in a mammal is provided. The method includes providing to a mammal in need thereof one or more signals having a continuous function or an aperiodic pulse train that increases heat shock protein expression and reduces pro-inflammatory cytokines in the mammal in need thereof.

In yet another embodiment of the present disclosure, a device for reducing inflammation in a mammal is provided. The device comprises a power supply, an amplifier, an antenna and a waveform generator where the device generates one or more signals having a continuous waveform function or an aperiodic pulse train that reduce inflammation in a mammal in need thereof.

In yet another embodiment of the present disclosure, a device for reducing inflammation in a mammal is provided. The device comprises a power supply, an amplifier, an antenna and a waveform generator, where the amplifier is an A-class linear or E-class low-power operating in the frequency range from $\frac{1}{100}^{th}$ Hz to 100 GHz.

In yet another embodiment of the present disclosure, a device for reducing inflammation in a mammal is provided. The device comprises a power supply, an amplifier, an antenna and a waveform generator configured to deliver light waves in the infrared, visible and ultraviolet frequency ranges.

In yet another embodiment of the present disclosure, a device for reducing inflammation in a mammal is provided. The device comprises a power supply, an amplifier, an antenna and a waveform generator configured to deliver mechanical vibrations in the frequency range from $\frac{1}{100}^{th}$ of a Hz to 30,000 Hz.

In yet another embodiment of the present disclosure, a device for reducing inflammation in a mammal is provided. The device comprises a power supply, an amplifier, an antenna, a battery and a waveform generator, where the device is battery powered.

In yet another embodiment of the present disclosure, a device for reducing inflammation in a mammal is provided. The device comprises a power supply, an amplifier, an antenna and a waveform generator, where the device is wearable.

In yet another embodiment of the present disclosure, a device for reducing inflammation in a mammal is provided. The device comprises a power supply, an amplifier, an antenna and a waveform generator, where the power supply is wireless.

In yet another embodiment of the present disclosure, a device for reducing inflammation in a mammal is provided. The device comprises a power supply, an amplifier, an antenna and a waveform generator, where the waveform generator is analog or digital operating from $\frac{1}{100}^{th}$ Hz to 100 MHz.

In yet another embodiment of the present disclosure, a device for reducing inflammation in a mammal is provided. The device comprises a power supply, an amplifier, an antenna and a waveform generator where the waveform generator is analog or digital operating in FCC-allocated Industrial Scientific and Medical (ISM) bands centered around 6.78, 13.56, 27.12 and 40.68 MHz.

In yet another embodiment of the present disclosure, a device for reducing inflammation in a mammal is provided. The device comprises a power supply, an amplifier, an antenna and a waveform generator where the waveform generator uses a digital synthesis module or crystal oscillator operating at 27.12 MHz.

In at least one aspect of at least one embodiment of the present disclosure, the one or more signals also has a variable local peak level or a non-constant repetition frequency.

In at least another aspect at of least one embodiment of the present disclosure, the one or more signals also have one or more features selected from the group of: variable intervals between successive stimulation events, variable pulse separation, with the interval between one or more of the stimulation events local peaks of the one or more signals provided to the mammal having a duration of approximately 10 nanoseconds to one second during a one-second treatment interval, an is modulated using aperiodic continuous waveform functions or a waveform with particular pulse separation intervals.

In at least another aspect at of least one embodiment of the present disclosure, the one or more signals also have at least two stimulation events delivered within a time interval of about 10 nanoseconds to 100 seconds.

In at least another aspect at of least one embodiment of the present disclosure, the one or more signals are nonrepeating within a time interval between about 10 nanoseconds to 100 seconds.

In at least another aspect at of least one embodiment of the present disclosure, the one or more signals delivers at least 400 stimulation events in a 1-second interval.

In at least another aspect at of least one embodiment of the present disclosure, the one or more signals provides eight stimulation events of 2 msec pulse duration at approximately 63.89 msec, 183.79 msec, 337.98 msec, 457.82 msec, 550.91 msec, 653.69 msec, 878.31 msec and 970.20 msec within the 1st second of the one or more signals provided.

In at least another aspect at of least one embodiment of the present disclosure, the one or more signals also have one or more features selected from the group of: a variable local peak level, a non-constant repetition frequency, variable intervals between successive stimulation events or variable pulse separation.

In at least another aspect of at least one embodiment of the present disclosure, the one or more signals also have one or more waveform features selected from measures of waveform complexity, frequency content and bandwidth.

In at least another aspect of at least one embodiment of the present disclosure, the one or more signals has waveform features selected from measures of: cell membrane potentials, inter-cellular signaling, cell and central nervous system neuronal signaling, cardiac and hypothalamic-pituitary-adrenal axis dynamics and other electrochemical pathways mediating inflammatory signaling activity.

In at least another aspect of at least one embodiment of the present disclosure, the one or more signals has waveform features measuring waveform time-windowed variance, irregularity of local peaks, self-similarity, fractal dimension and scaling dynamics.

In at least another aspect of at least one embodiment of the present disclosure, the one or more signals has waveform features derived from the Larmor, cyclotron and spin-precession frequencies characteristic of ion resonance dynamics and radical pair recombination lifetimes.

In at least another aspect of at least one embodiment of the present disclosure, the one or more signals also have features selected from the group of: the interval between one or more of the stimulation events local peaks of the one or more signals provided to the mammal have a duration of approximately 10 nanoseconds to one second during a one-second treatment interval, the one or more signals generated is modulated using aperiodic continuous waveform functions and/or particular pulse separation intervals, the one or more signals have at least two stimulation events delivered within a time interval of about 10 nanoseconds to 100 seconds or the one or more signals are nonrepeating within a time interval between about 10 nanoseconds to 100 seconds.

In at least another aspect of at least one embodiment of the present disclosure, the one or more signals delivers at least 400 stimulation events in a 1-second interval.

In at least another aspect of at least one embodiment of the present disclosure, the one or more signals also have at least three stimulation events delivered within about 10 nanoseconds to 100 seconds with different time intervals between each of the components of the one or more signals.

In at least another aspect of at least one embodiment of the present disclosure, the one or more signals also have at least three stimulation events delivered within about 1 second with different time intervals between each of the components.

In at least another aspect of at least one embodiment of the present disclosure, the one or more signals also have at least three stimulation events with unequal local peak levels delivered within about 10 nanoseconds to 100 seconds.

In at least another aspect of at least one embodiment of the present disclosure, the one or more signals also have at least three stimulation events with unequal local peak levels delivered within about 10 nanoseconds to 1 hour.

In at least another aspect of at least one embodiment of the present disclosure, the one or more signals are nonrepeating within a time interval for the one or more signals between about 10 nanoseconds to 100 seconds.

In at least another aspect of at least one embodiment of the present disclosure, the one or more signals are nonrepeating within a time interval for the one or more signals between about 10 nanoseconds to 1 hour.

In at least one aspect of at least one embodiment of the present disclosure, the one or more signals is delivered using an antenna configured for direct electrode contact.

In at least one aspect of at least one embodiment of the present disclosure, the one or more signals is delivered using an antenna configured for capacitive electric coupling.

In at least one aspect of at least one embodiment of the present disclosure, the one or more signals is delivered using an antenna configured for optical stimulation using light waves in the infrared, visible and ultraviolet frequency ranges.

In at least one aspect of at least one embodiment of the present disclosure, the one or more signals is delivered using an antenna configured for broadcasting mechanical vibrations in the frequency range from $\frac{1}{100}^{th}$ of a Hz to 30,000 Hz.

In at least one aspect of at least one embodiment of the present disclosure, the one or more signals has features characteristic of the time-varying dynamics exhibited by one or more of: inflammatory cytokine signaling pathways; ion transport pathways; microtubule transport pathways; cell membrane potentials; inter-cellular signaling; vascular endothelial electrochemical network signaling; cardiac electrical activity; brain and central nervous system signaling; tissue, organ and whole-body electrical potentials; hypothalamic pituitary adrenal axis dynamics; circadian cycles.

The data and results of the experiments disclosed herein demonstrate that new devices, methods and signals disclosed herein increase heat shock protein expression and reduce inflammation and inflammatory cytokines significantly more than previous FDA-cleared signals by employing the particular signals having the waveform features described herein.

What is claimed is:

1. A method comprising providing one or more electromagnetic field signals having an aperiodic continuous waveform or an aperiodic pulse train to a mammal, wherein the one or more electromagnetic field signals increase heat shock protein expression in the mammal.

2. The method of claim 1, wherein the one or more electromagnetic field signals deliver a plurality of stimulation events having variable intervals between successive stimulation events.

3. The method claim 1, wherein the one or more electromagnetic field signals deliver at least two stimulation events that have peak amplitudes separated by 10 nanoseconds to one second.

4. The method of claim 1, wherein the one or more electromagnetic field signals deliver eight stimulation events at 63.89 msec, 183.79 msec, 337.98 msec, 457.82 msec, 550.91 msec, 653.69 msec, 878.31 msec, and 970.20 msec within the first second of delivery.

5. The method of claim 1, wherein the one or more electromagnetic field signals deliver at least 400 stimulation events during a one second interval.

6. The method of claim 1, wherein the one or more electromagnetic field signals deliver at least three stimulation events that each have a different peak amplitude.

7. The method of claim 1, wherein the one or more electromagnetic field signals delivers at least three stimulation events during a time period of from 10 nanoseconds to 1 hour.

8. The method of claim 1, wherein the one or more electromagnetic field signals are delivered with a peak magnetic field level between 50 pT and 200 µT.

9. The method of claim 1, wherein the one or more electromagnetic field signals are delivered with two or more local peak magnetic field levels, wherein a local peak magnetic field level of the two or more local peak magnetic field levels is less than 10 µT.

10. The method of claim 1, wherein the one or more electromagnetic field signals also reduce inflammation in the mammal by reducing pro-inflammatory cytokines.

11. The method of claim 1, wherein a frequency of the one or more electromagnetic field signals is between $\frac{1}{100}$ Hz and 100 MHz.

12. The method of claim 1, wherein the one or more electromagnetic field signals are generated using one or more aperiodic continuous waveform functions or one or more pulse separation intervals.

13. The method of claim 1, wherein the one or more electromagnetic field signals deliver at least two stimulation events to the mammal within a time interval between 10 nanoseconds and 100 seconds.

14. The method of claim 1, wherein the one or more electromagnetic field signals deliver at least eight stimulation events that each have a 2 msec pulse duration.

* * * * *